US011124495B2

(12) United States Patent
Cheng et al.

(10) Patent No.: US 11,124,495 B2
(45) Date of Patent: Sep. 21, 2021

(54) TETRAHYDROISOQUINOLINES AND TERAHYDRONAPHTHYRIDINES FOR THE TREATMENT OF HEPATITIS B VIRUS INFECTION

(71) Applicant: Hoffmann-La Roche Inc., Little Falls, NJ (US)

(72) Inventors: Zhanling Cheng, Shanghai (CN); Jianhua Wang, Shanghai (CN); Min Wang, Shanghai (CN); Song Yang, Shanghai (CN)

(73) Assignee: Hoffmann-La Roche, Inc., Little Falls, NJ (US)

( * ) Notice: Subject to any disclaimer, the term of this patent is extended or adjusted under 35 U.S.C. 154(b) by 0 days.

(21) Appl. No.: 16/346,778

(22) PCT Filed: Nov. 2, 2017

(86) PCT No.: PCT/EP2017/077992
§ 371 (c)(1),
(2) Date: May 1, 2019

(87) PCT Pub. No.: WO2018/083136
PCT Pub. Date: May 11, 2018

(65) Prior Publication Data
US 2019/0276433 A1   Sep. 12, 2019

(30) Foreign Application Priority Data

Nov. 3, 2016   (WO) ................ PCT/CN2016/104439

(51) Int. Cl.
*C07D 401/14* (2006.01)
*A61P 31/20* (2006.01)
*C07D 471/04* (2006.01)

(52) U.S. Cl.
CPC ............ *C07D 401/14* (2013.01); *A61P 31/20* (2018.01); *C07D 471/04* (2013.01)

(58) Field of Classification Search
CPC ........................... A61K 31/506; C07D 401/14

USPC .......................................... 514/256; 544/296
See application file for complete search history.

(56) References Cited

FOREIGN PATENT DOCUMENTS

| WO | 2012/055942 A1 | 5/2012 |
| WO | 2015/113990 A1 | 8/2015 |
| WO | 2015/145322 A1 | 10/2015 |
| WO | 2015/173164 A1 | 11/2015 |
| WO | 2016/023877 A1 | 2/2016 |
| WO | 2016/071215 A1 | 5/2016 |
| WO | 2016/107832 A1 | 7/2016 |
| WO | 2016/128335 A1 | 8/2016 |
| WO | 2016/177655 A1 | 11/2016 |

OTHER PUBLICATIONS

International Preliminary Report on Patentability—PCT/EP2017/077992 dated May 7, 2020.
International Search Report—PCT/EP2017/077992 dated Dec. 15, 2017.

*Primary Examiner* — Jeffrey H Murray
(74) *Attorney, Agent, or Firm* — Genentech, Inc.; Richard G. A. Bone

(57) ABSTRACT

The present invention provides novel compounds having the general formula (I): wherein $R^1$, $R^2$, $R^3$, U, V, W, X and Y are as described herein, compositions including the compounds and methods of using the compounds.

19 Claims, No Drawings

TETRAHYDROISOQUINOLINES AND TERAHYDRONAPHTHYRIDINES FOR THE TREATMENT OF HEPATITIS B VIRUS INFECTION

CROSS-REFERENCE TO RELATED APPLICATIONS

This application is a National Stage Entry of PCT Application No. PCT/EP2017/077992, filed on Nov. 2, 2017, which claims benefit of priority to International Application No. PCT/CN2016/104439, filed on Nov. 3, 2016, all of which are incorporated herein by reference in their entirety.

The present invention relates to organic compounds useful for therapy and/or prophylaxis in a mammal, and in particular to $HB_sAg$ (HBV Surface antigen) inhibitors and HBV DNA production inhibitors useful for treating HBV infection.

FIELD OF THE INVENTION

The present invention relates to novel tetrahydroisoquinolines and terahydronaphthyridines having pharmaceutical activity, their manufacture, pharmaceutical compositions containing them and their potential use as medicaments.

The present invention relates to compounds of formula I

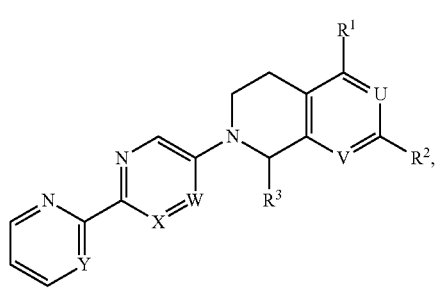

(I)

wherein $R^1$, $R^2$, $R^3$, U, V, W, X and Y are as described below, or pharmaceutically acceptable salts, or enantiomers, or diastereomers thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. Hepatology, 46, (2007), 1759-68) and via the specific binding of HBV surface antigens (HBsAg) to the hepatocyte sodium-taurocholate cotransporting polypeptide (NTCP) receptor (Yan, H. et al. J Virol, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. J Viral Hepat, 17, (2010), 527-36). Inhibition of HBV gene expression or HBV RNA synthesis leads to the inhibition of HBV viral replication and antigens production (Mao, R. et al. PLoS Pathog, 9, (2013), e1003494; Mao, R. et al. J Virol, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. J Clin Invest, 122, (2012), 529-37; Mao, R. et al. J Virol, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. Semin Liver Dis, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. Virol J, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433; Fisicaro et al. *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat.* (2012), 19, e26-33; Kondo et al. *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94).

A few patent applications for HBsAg inhibitors have been published, including novel dihydroquinolizinones (WO 2015/113990, WO 2015/173164), novel pyridazones and triazinones (WO2016/023877), novel 6,7-dihydrobenzo[a] quinolizin-2-one derivatives (WO/2016/071215), novel tetrahydropyridopyrimidines and tetrahydropyridopyridines (WO2016/107832) and novel 2-oxo-6,7-dihydrobenzo[a] quinolizine-3 carboxylic acid derivatives (WO 2016/128335), showing that there are some earlier exploratory efforts ongoing in this field. However, there is no commercial product approved. Therefore, there is an unmet medical need to target HBsAg for HBV treatment (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

Objects of the present invention are novel compounds of formula I, their manufacture, medicaments based on a compound in accordance with the invention and their production as well as the use of compounds of formula I as HBV inhibitors and for the treatment or prophylaxis of HBV infection. The compounds of formula I show superior anti-HBV activity.

The present invention relates to a compound of formula I

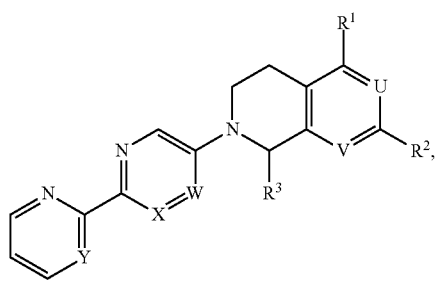

(I)

Wherein
$R^1$ and $R^2$ are independently selected from amino, aminocarbonyC$_{1-6}$alkoxy, aminocarbonyC$_{1-6}$alkoxy, carboxy C$_{1-6}$alkoxy, C$_{1-6}$alkoxy, C$_{1-6}$alkoxyC$_{1-6}$alkyl, C$_{1-6}$alkoxyC$_{3-7}$cycloalkyl, C$_{1-6}$alkyl, C$_{1-6}$alkylamino, C$_{1-6}$alkylC$_{3-7}$cycloalkyl, C$_{3-7}$cycloalkoxy, C$_{3-7}$cycloalkyl, C$_{3-7}$cycloalkylC$_{1-6}$alkoxy, cyano, diC$_{1-6}$alkylamino, haloC$_{1-6}$alkoxy, haloC$_{1-6}$alkyl, halogen and hydrogen;
$R^3$ is C$_{1-6}$alkyl, C$_{3-7}$cycloalkyl or hydrogen;
U is N or CR$^4$, wherein R$^4$ is C$_{1-6}$alkoxy, C$_{1-6}$alkyl, C$_{3-7}$cycloalkoxy, C$_{3-7}$cycloalkyl, C$_{1-6}$alkylamino, cyano, diC$_{1-6}$alkylamino, haloC$_{1-6}$alkoxy, haloC$_{1-6}$alkyl, halogen or hydrogen;
V is N or CR$^5$, wherein R$^5$ is C$_{1-6}$alkyl, C$_{3-7}$cycloalkyl or hydrogen;
W, X and Y are independently selected from N or CH;
or pharmaceutically acceptable salts, or enantiomers, or diastereomers thereof.

DETAILED DESCRIPTION OF THE INVENTION

Definitions

As used herein, the term "C$_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "C$_{1-6}$alkyl" groups are methyl, ethyl, isopropyl and tert-butyl.

The term "C$_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "C$_{3-7}$cycloalkyl" groups are cyclopropyl, cyclobutyl, cyclopentyl and cyclohexyl.

The term "C$_{1-6}$alkoxy" alone or in combination signifies a group C$_{1-6}$alkyl-O—, wherein the "C$_{1-6}$alkyl" is as defined above; for example methoxy, ethoxy, propoxy, iso-propoxy, n-butoxy, iso-butoxy, 2-butoxy, tert-butoxy, pentoxy, hexyloxy and the like. Particular "C$_{1-6}$alkoxy" groups are methoxy, ethoxy and propoxy.

The term "halogen" means fluorine, chlorine, bromine or iodine.

The term "haloC$_{1-6}$alkyl" denotes a C$_{1-6}$alkyl group wherein at least one of the hydrogen atoms of the C$_{1-6}$alkyl group has been replaced by same or different halogen atoms, particularly fluoro atoms. Examples of haloC$_{1-6}$alkyl include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "haloC$_{1-6}$alkyl" group is difluoromethyl or trifluoromethyl.

The term "haloC$_{1-6}$alkoxy" denotes a C$_{1-6}$alkoxy group wherein at least one of the hydrogen atoms of the C$_{1-6}$alkoxy group has been replaced by same or different halogen atoms, particularly fluoro atoms. Examples of haloC$_{1-6}$alkoxyl include monofluoro-, difluoro- or trifluoro-methoxy, -ethoxy or -propoxy, for example fluoropropoxy, difluoropropoxy, trifluoropropoxy, fluoroethoxy, difluoroethoxy, trifluoroethoxy, fluoromethoxy, difluoromethoxy or trifluoromethoxy. Particular "haloC$_{1-6}$alkoxy" group is 3-fluoropropoxy, 3,3-difluoropropoxy, 3,3,3-trifluoropropoxy, 2-fluoroethoxy, 2,2-difluoroethoxy, 2,2,2-trifluoroethoxy, fluoromethoxy, difluoromethoxy or trifluoromethoxy.

The term "amino" denotes a group of the formula —NR'R" wherein R' and R" are independently hydrogen, $C_{1-6}$alkyl, $C_{1-6}$alkoxy, $C_{3-7}$cycloalkyl, hetero$C_{3-7}$cycloalkyl, aryl or heteroaryl. Alternatively, R' and R", together with the nitrogen to which they are attached, can form a hetero $C_{3-7}$cycloalkyl.

The term "carbonyl" alone or in combination refers to the group —C(O)—.

The term "cyano" alone or in combination refers to the group —CN.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBsAg

The present invention provides (i) a compound having the general formula I:

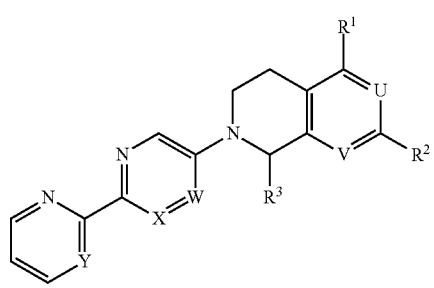

(I)

wherein $R^1$ and $R^2$ are independently selected from amino, aminocarbony$C_{1-6}$alkoxy, aminocarbony$C_{1-6}$alkoxy, carboxy $C_{1-6}$alkoxy, $C_{1-6}$alkoxy, $C_{1-6}$alkoxy$C_{1-6}$alkyl, $C_{1-6}$alkoxy$C_{3-7}$cycloalkyl, $C_{1-6}$alkyl, $C_{1-6}$alkylamino, $C_{1-6}$alkyl$C_{3-7}$cycloalkyl, $C_{3-7}$cycloalkoxy, $C_{3-7}$cycloalkyl, $C_{3-7}$cycloalkyl$C_{1-6}$alkoxy, cyano, di$C_{1-6}$alkylamino, halo$C_{1-6}$alkoxy, halo$C_{1-6}$alkyl, halogen and hydrogen;

$R^3$ is $C_{1-6}$alkyl, $C_{3-7}$cycloalkyl or hydrogen;

U is N or $CR^4$, wherein $R^4$ is $C_{1-6}$alkoxy, $C_{1-6}$alkyl, $C_{3-7}$cycloalkoxy, $C_{3-7}$cycloalkyl, $C_{1-6}$alkylamino, cyano, di$C_{1-6}$alkylamino, halo$C_{1-6}$alkoxy, halo$C_{1-6}$alkyl, halogen or hydrogen;

V is N or $CR^5$, wherein $R^5$ is $C_{1-6}$alkyl, $C_{3-7}$cycloalkyl or hydrogen;

W, X and Y are independently selected from N or CH;

or pharmaceutically acceptable salts, or enantiomers, or diastereomers thereof.

A further embodiment of the present invention is (ii) a compound of formula I, wherein $R^1$ and $R^2$ are independently selected from aminocarbony $C_{1-6}$alkoxy, $C_{1-6}$alkoxy, $C_{1-6}$alkoxy$C_{3-7}$cycloalkyl, $C_{1-6}$alkyl, $C_{1-6}$alkylamino, $C_{3-7}$cycloalkyl, $C_{3-7}$cycloalkyl$C_{1-6}$alkoxy, cyano, di$C_{1-6}$alkylamino, halo$C_{1-6}$alkoxy, halogen and hydrogen;

$R^3$ is $C_{1-6}$alkyl or hydrogen;

U is N or $CR^4$, wherein $R^4$ is $C_{1-6}$alkoxy, $C_{3-7}$cycloalkyl, di$C_{1-6}$alkylamino, halogen or hydrogen;

V is N or CH;

W, X and Y are independently selected from N or CH;

or pharmaceutically acceptable salts, or enantiomers, or diastereomers thereof.

Another embodiment of the present invention is (iii) a compound of formula I, wherein, $R^1$ and $R^2$ are independently selected from aminocarbonylmethoxy, methoxy, methoxycyclobutyl, methyl, methylamino, cyclopropyl, cyclopropylmethoxy, cyano, dimethylamino, difluoroethoxy, chloro, fluoro and hydrogen;

$R^3$ is ethyl, methyl or hydrogen;

U is N or $CR^4$, wherein $R^4$ is methoxy, cyclopropyl, dimethylamino, chloro, fluoro or hydrogen;

V is N or CH;

W, X and Y are independently selected from N or CH;

or pharmaceutically acceptable salts, or enantiomers, or diastereomers thereof.

A further embodiment of the present invention is (iv) a compound of formula I, or pharmaceutically acceptable salts, or enantiomers, or diastereomers thereof, wherein $R^1$ is $C_{1-6}$alkoxy, halogen or hydrogen; and all remaining substituents have the significances given herein before.

Another embodiment of the present invention is (v) a compound of formula I, or pharmaceutically acceptable salts, or enantiomers, or diastereomers thereof, wherein $R^1$ is methoxy, chloro, fluoro or hydrogen; and all remaining substituents have the significances given herein before.

A further embodiment of the present invention is (vi) a compound of formula I, or pharmaceutically acceptable salts, or enantiomers, or diastereomers thereof, wherein $R^2$ is $C_{1-6}$alkoxy, $C_{3-7}$cycloalkyl$C_{1-6}$alkoxy, halo$C_{1-6}$alkoxy, halogen or hydrogen; and all remaining substituents have the significances given herein before.

A further embodiment of the present invention is (vii) a compound of formula I, or pharmaceutically acceptable salts, or enantiomers, or diastereomers thereof, wherein $R^2$ is methoxy, cyclopropylmethoxy, difluoroethoxy, chloro, fluoro or hydrogen; and all remaining substituents have the significances given herein before.

A further embodiment of the present invention is (viii) a compound of formula I, or pharmaceutically acceptable salts, or enantiomers, or diastereomers thereof, wherein $R^3$ is hydrogen; and all remaining substituents have the significances given herein before.

Another embodiment of the present invention is (ix) a compound of formula I, or pharmaceutically acceptable salts, or enantiomers, or diastereomers thereof, wherein U is CH; V is CH; W is CH; X is N; Y is N; and all remaining substituents have the significances given herein before.

A further embodiment of the present invention is (x) a compound of formula I, wherein
$R^1$ is $C_{1-6}$alkoxy or halogen;
$R^2$ is $C_{1-6}$alkoxy, $C_{3-7}$cycloalkyl$C_{1-6}$alkoxy, halo$C_{1-6}$alkoxy or halogen;
$R^3$ is $C_{1-6}$alkyl or hydrogen;
U is CH;
V is CH;
W is CH;
X is N;
Y is N;
or pharmaceutically acceptable salts, or enantiomers, or diastereomers thereof.

Another embodiment of the present invention is (xi) a compound of formula I, wherein
$R^1$ is methoxy, chloro or fluoro;
$R^2$ is methoxy, cyclopropylmethoxy, difluoroethoxy or chloro;
$R^3$ is methyl or hydrogen;
U is CH;
V is CH;
W is CH;
X is N;
Y is N;
or pharmaceutically acceptable salts, or enantiomers, or diastereomers thereof.

Particular compounds of formula I according to the invention are the following:
2-(2-Pyrimidin-2-ylpyrimidin-5-yl)-3,4-dihydro-1H-isoquinoline;
7-Fluoro-2-(2-pyrimidin-2-ylpyrimidin-5-yl)-3,4-dihydro-1H-isoquinoline;
6,7-Dimethoxy-2-(2-pyrimidin-2-ylpyrimidin-5-yl)-3,4-dihydro-1H-isoquinoline;
6-Methoxy-2-(2-pyrimidin-2-ylpyrimidin-5-yl)-3,4-dihydro-1H-isoquinoline;
5-Fluoro-7-methoxy-2-(2-pyrimidin-2-ylpyrimidin-5-yl)-3,4-dihydro-1H-isoquinoline;
7-Fluoro-5-methoxy-2-(2-pyrimidin-2-ylpyrimidin-5-yl)-3,4-dihydro-1H-isoquinoline;
5-Fluoro-7-methoxy-1-methyl-2-(2-pyrimidin-2-ylpyrimidin-5-yl)-3,4-dihydro-1H-isoquinoline;
5-Fluoro-7-methoxy-2-(5-pyrimidin-2-ylpyrazin-2-yl)-3,4-dihydro-1H-isoquinoline;
6-Chloro-2-(2-pyrimidin-2-ylpyrimidin-5-yl)-3,4-dihydro-1H-isoquinoline;
6,7-Dimethoxy-2-[6-(2-pyridyl)-3-pyridyl]-3,4-dihydro-1H-isoquinoline;
6-Fluoro-2-(2-pyrimidin-2-ylpyrimidin-5-yl)-3,4-dihydro-1H-isoquinoline;
2-Methoxy-7-(pyrimidin-2-ylpyrimidin-5-yl)-6,8-dihydro-5H-1,7-naphthyridine;
7-Methoxy-2-(2-pyrimidin-2-ylpyrimidin-5-yl)-3,4-dihydro-1H-2,6-naphthyridine;
7-Methoxy-2-(2-pyrimidin-2-ylpyrimidin-5-yl)-3,4-dihydro-1H-isoquinoline;
7-Cyclopropyl-2-(2-pyrimidin-2-ylpyrimidin-5-yl)-3,4-dihydro-1H-isoquinoline;
N,N-Dimethyl-2-(2-pyrimidin-2-ylpyrimidin-5-yl)-3,4-dihydro-1H-isoquinolin-7-amine;
7-Methyl-2-(2-pyrimidin-2-ylpyrimidin-5-yl)-3,4-dihydro-1H-isoquinoline;
N-Methyl-2-(2-pyrimidin-2-ylpyrimidin-5-yl)-3,4-dihydro-1H-isoquinolin-7-amine;
7-(2,2-Difluoroethoxy)-5-fluoro-2-(2-pyrimidin-2-ylpyrimidin-5-yl)-3,4-dihydro-1H-isoquinoline;
2-(2-Pyrimidin-2-ylpyrimidin-5-yl)-3,4-dihydro-1H-isoquinoline-7-carbonitrile;
7-(Cyclopropylmethoxy)-5-fluoro-2-(2-pyrimidin-2-ylpyrimidin-5-yl)-3,4-dihydro-1H-isoquinoline;
7-Chloro-2-(2-pyrimidin-2-ylpyrimidin-5-yl)-3,4-dihydro-1H-isoquinoline;
N,N-Dimethyl-2-(2-pyrimidin-2-ylpyrimidin-5-yl)-3,4-dihydro-1H-isoquinolin-6-amine;
6-Cyclopropyl-2-(2-pyrimidin-2-ylpyrimidin-5-yl)-3,4-dihydro-1H-isoquinoline;
2-(2-Pyrimidin-2-ylpyrimidin-5-yl)-3,4-dihydro-1H-isoquinoline-5-carbonitrile;
7-(3-Methoxycyclobutyl)-2-(2-pyrimidin-2-ylpyrimidin-5-yl)-3,4-dihydro-1H-isoquinoline;
5-Fluoro-2-(2-pyrimidin-2-ylpyrimidin-5-yl)-3,4-dihydro-1H-isoquinoline;
2-[[5-Fluoro-2-(2-pyrimidin-2-ylpyrimidin-5-yl)-3,4-dihydro-1H-isoquinolin-7-yl]oxy]acetamide;
5-Cyclopropyl-2-(2-pyrimidin-2-ylpyrimidin-5-yl)-3,4-dihydro-1H-isoquinoline;
N,N-Dimethyl-2-(2-pyrimidin-2-ylpyrimidin-5-yl)-3,4-dihydro-1H-isoquinolin-5-amine;
5-Chloro-7-methoxy-2-(2-pyrimidin-2-ylpyrimidin-5-yl)-3,4-dihydro-1H-isoquinoline;
7-Chloro-5-methoxy-2-(2-pyrimidin-2-ylpyrimidin-5-yl)-3,4-dihydro-1H-isoquinoline; and
1-Ethyl-5-fluoro-7-methoxy-2-(2-pyrimidin-2-ylpyrimidin-5-yl)-3,4-dihydro-1H-isoquinoline;
or pharmaceutically acceptable salts, or enantiomers, or diastereomers thereof.

More particularly, the invention relates to the following compounds of formula I:
5-Fluoro-7-methoxy-2-(2-pyrimidin-2-ylpyrimidin-5-yl)-3,4-dihydro-1H-isoquinoline;
5-Fluoro-7-methoxy-1-methyl-2-(2-pyrimidin-2-ylpyrimidin-5-yl)-3,4-dihydro-1H-isoquinoline;
7-(2,2-Difluoroethoxy)-5-fluoro-2-(2-pyrimidin-2-ylpyrimidin-5-yl)-3,4-dihydro-1H-isoquinoline;
7-(Cyclopropylmethoxy)-5-fluoro-2-(2-pyrimidin-2-ylpyrimidin-5-yl)-3,4-dihydro-1H-isoquinoline;
5-Chloro-7-methoxy-2-(2-pyrimidin-2-ylpyrimidin-5-yl)-3,4-dihydro-1H-isoquinoline; and
7-Chloro-5-methoxy-2-(2-pyrimidin-2-ylpyrimidin-5-yl)-3,4-dihydro-1H-isoquinoline;
or pharmaceutically acceptable salts, or enantiomers, or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$, $R^2$, $R^3$, U, V, W, X and Y are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Compound Ia and Ic (Scheme 1)

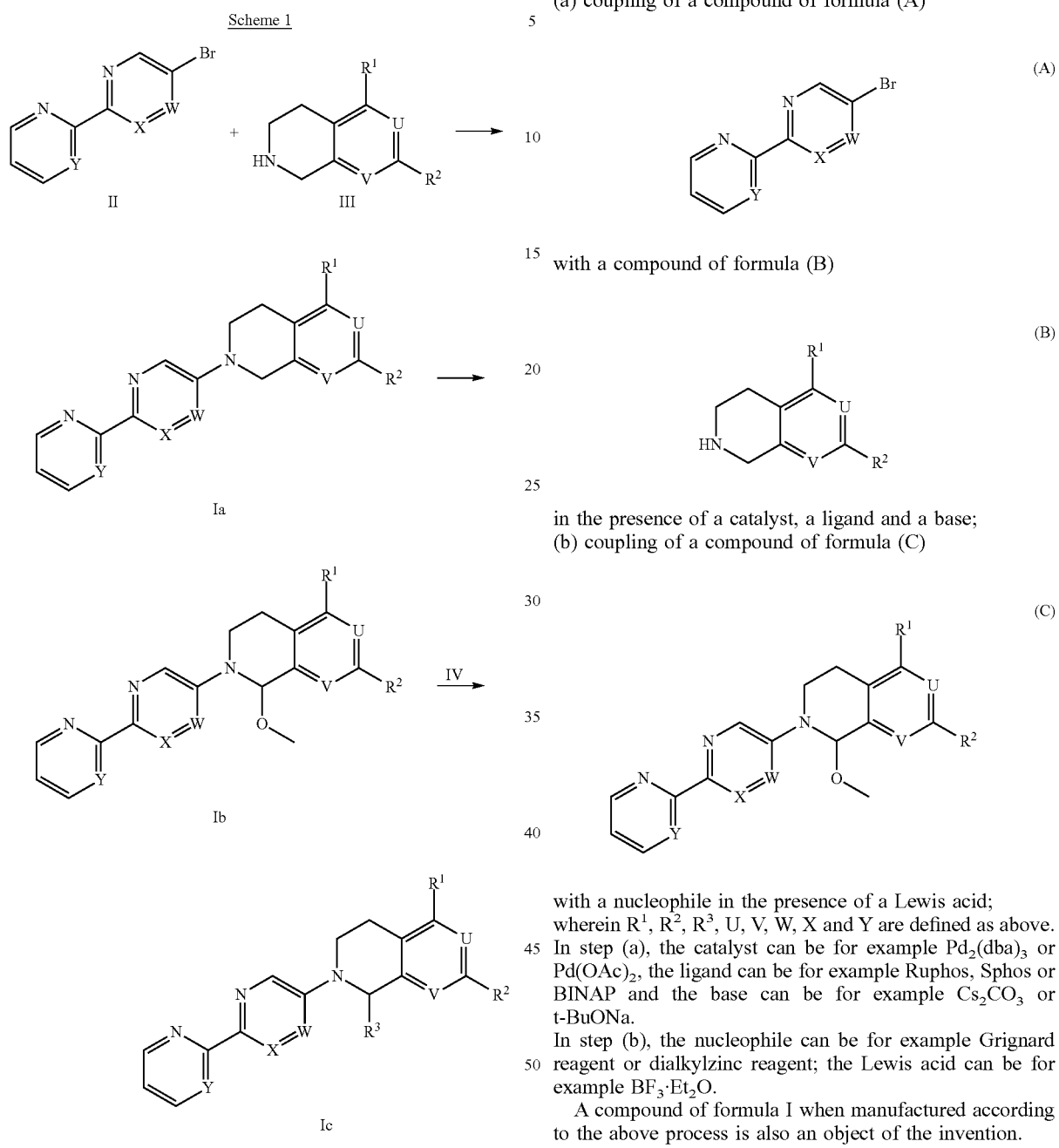

The compound of formula Ia and Ic can be prepared according to Scheme 1.

Compound II is coupled with compound III in the presence of a catalyst such as $Pd_2(dba)_3$ or $Pd(OAc)_2$, a ligand such as Ruphos, Sphos or BINAP and a base such as $Cs_2CO_3$ or t-BuONa in a suitable solvent such as 1, 4-dioxane or toluene, to afford compound Ia. Oxidation of compound Ia with a suitable oxidant such as NBS in the presence of MeOH generates intermediate Ib. Reaction of compound Ib with a suitable nucleophile IV such as Grignard reagent or dialkylzinc reagent, in the presence of a Lewis acid such as $BF_3 \cdot Et_2O$ produces compound Ic.

This invention also relates to a process for the preparation of a compound of formula I comprising one of the following steps:
(a) coupling of a compound of formula (A)

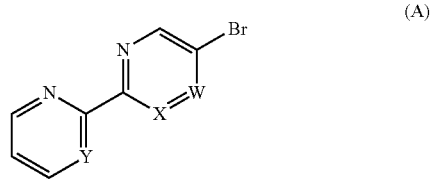

with a compound of formula (B)

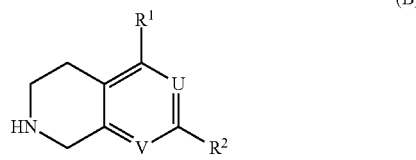

in the presence of a catalyst, a ligand and a base;
(b) coupling of a compound of formula (C)

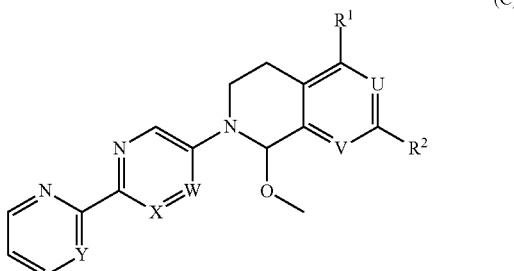

with a nucleophile in the presence of a Lewis acid;
wherein $R^1$, $R^2$, $R^3$, U, V, W, X and Y are defined as above.
In step (a), the catalyst can be for example $Pd_2(dba)_3$ or $Pd(OAc)_2$, the ligand can be for example Ruphos, Sphos or BINAP and the base can be for example $Cs_2CO_3$ or t-BuONa.
In step (b), the nucleophile can be for example Grignard reagent or dialkylzinc reagent; the Lewis acid can be for example $BF_3 \cdot Et_2O$.
A compound of formula I when manufactured according to the above process is also an object of the invention.
The compound of this invention also shows good safety and PK profile.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

EXAMPLES

The invention will be more fully understood by reference to the following examples. They should not, however, be construed as limiting the scope of the invention.
Abbreviations used herein are as follows:
μL: microliter
μm: micrometer
μM: micromoles per liter
$IC_{50}$: the half maximal inhibitory concentration
LC/MS: liquid chromatography/mass spectrometry
M: molarity
MHz: megahertz
min: minute
hr(s): hour(s)
mM: millimoles per liter
MS (ESI): mass spectroscopy (electron spray ionization)
NMR: nuclear magnetic resonance
obsd. observed
rt: room temperature
Pd/C: palladium on activated carbon
$Pd(PPh_3)_4$: tetrakis(triphenylphosphine)palladium(0)
$Pd_2(dba)_3$: Tris(dibenzylideneacetone)dipalladium(0)
$Pd(OAc)_2$: Palladium(II) acetate
NBS: N-bromosuccinimide
TFA: trifluoroacetic acid
δ: chemical shift
RuPhos: 2-dicyclohexylphosphino-2',6'-diisopropoxybiphenyl
BINAP: (2,2'-bis(diphenylphosphino)-1,1'-binaphthyl)
Sphos: 2-dicyclohexylphosphino-2',6'-dimethoxybiphenyl
t-BuONa: sodium tert-butoxide
DIPEA: N, N-diisopropylamine
tert-BuXPhos Pd G3: [(2-Di-tert-butylphosphino-2',4',6'-triisopropyl-1,1'-biphenyl)-2-(2'-amino-1,1'-biphenyl)] palladium(II) methanesulfonate
Brettphos Pd G3: [(2-Di-cyclohexylphosphino-3,6-dimethoxy-2',4',6'-triisopropyl-1,1'-biphenyl)-2-(2'-amino-1, 1'-biphenyl)]palladium(II) methanesulfonate methanesulfonate
tert-$Bu_3$P Pd G2: Chloro[(tri-tert-butylphosphine)-2-(2-aminobiphenyl)] palladium(II)
cataCXium® A Pd G2: Chloro[(di(1-adamantyl)-N-butylphosphine)-2-(2-aminobiphenyl)] palladium(II)
EA: ethyl acetate
General Experimental Conditions
Intermediates and final compounds were purified by flash chromatography using one of the following instruments: i) Biotage SPI system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

Chiral Separation was conducted on Thar 350 preparative SFC using ChiralPak AD-10u (200×50 mm I.D.) with mobile phase A for $CO_2$ and B for ethanol.

LC/MS spectra were obtained using an Acquity Ultra Performance LC—3100 Mass Detector or Acquity Ultra Performance LC—SQ Detector. Standard LC/MS conditions were as follows (running time 3 minutes):

Acidic condition: A: 0.1% formic acid in $H_2O$; B: 0.1% formic acid in acetonitrile;

Basic condition: A: 0.05% $NH_3$—$H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty or CEM Discover.

NMR Spectra were obtained using Bruker Avance 400 MHz.

All reactions involving air-sensitive reagents were performed under an argon atmosphere.

Reagents were used as received from commercial suppliers without further purification unless otherwise noted.

PREPARATIVE EXAMPLES

Example 1

2-(2-Pyrimidin-2-ylpyrimidin-5-yl)-3,4-dihydro-1H-isoquinoline

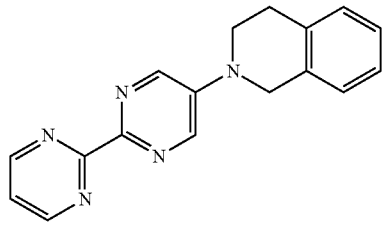 [SMILES: c1cnc(-c2ncc(N3CCc4ccccc4C3)cn2)nc1]

Step 1: Preparation of 4-bromopyrazol-1-amine

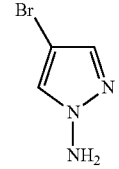

To a solution of 4-bromopyrazole (50.0 g, 340.21 mmol) in NaOH (500 mL, 4 N) was added hydroxylamine-O-sulfonic acid (115.4 g, 1021 mmol). The resulting mixture was heated and stirred at 50° C. for 16 hrs and then extracted with DCM (200 mL) for three times. The combined organic layer was washed with NaOH (200 mL, 4N), dried over anhydrous $Na_2SO_4$ and concentrated in vacuo to give 4-bromopyrazol-1-amine (40.0 g, crude) as off white solid, which was used in the next step without any further purification.

Step 2: Preparation of 5-bromotriazine

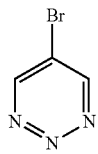

A solution of crude 4-bromopyrazol-1-amine (20.0 g, crude) in DCM (500 mL) and water (200 mL) was cooled to 0° C. To the solution was added NaIO$_4$ (52.8 g, 246.93 mmol). The resulting mixture was stirred at 0° C. for 4 hrs and extracted with DCM (100 mL) for three times. The combined organic layer was washed with brine (100 mL), dried over anhydrous Na$_2$SO$_4$ and concentrated in vacuo to give 5-bromotriazine (20.0 g) as brown solid, which was used in next step directly without any further purification.

Step 3: Preparation of 5-bromo-2-pyrimidin-2-yl-pyrimidine

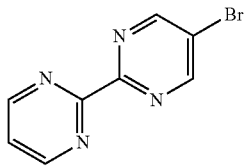 [SMILES: Brc1cnc(-c2ncccn2)nc1]

To a solution of 5-bromotriazine (20.0 g, crude) in 1,4-dioxane (600 mL) was added pyrimidine-2-carboxamidine (16.8 g, 137.53 mmol) at 0° C. After being stirred at 0° C. for 1 hrs, the resulting mixture was warmed to 30° C. and stirred at 30° C. for 1 hr, and then filtered. The filtrate was concentrated in vacuo. The residue was diluted with H$_2$O (500 mL) and extracted with DCM (500 mL) for three times. The combined organic layer was washed with brine (1.0 L), dried over anhydrous Na$_2$SO$_4$ and concentrated in vacuo. The residue was purified on silica gel column (eluting with DCM/MeOH=10/1, v:v) to give 5-bromo-2-pyrimidin-2-yl-pyrimidine (9.0 g) as yellow solid.

Step 4: Preparation of 2-(2-pyrimidin-2-ylpyrimidin-5-yl)-3,4-dihydro-1H-isoquinoline

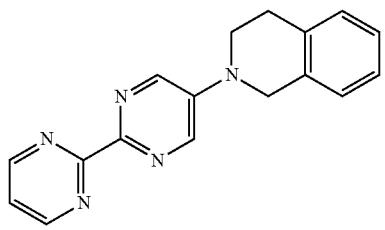 [SMILES: c1cnc(-c2ncc(N3CCc4ccccc4C3)cn2)nc1]

A flask containing a mixture of 5-bromo-2-pyrimidin-2-yl-pyrimidine (300 mg, 1.27 mmol), 1,2,3,4-tetrahydroisoquinoline (337 mg, 2.53 mmol) and sodium tert-butoxide (243 mg, 2.53 mmol) in toluene (15 mL) was degassed and charged with N$_2$. To the mixture was added Ruphos (23.6 mg, 50.6 μmol) and Pd$_2$(dba)$_3$ (23.2 mg, 25.3 μmol). After being heated to 120° C. with stirring 4 hrs, the resulting mixture was cooled to rt, then diluted with saturated aqueous NH$_4$Cl solution and extracted with DCM (50 mL) for three times. The combined organic layer was dried over Na$_2$SO$_4$ and concentrated in vacuo. The residue was purified by prep-HPLC to give 2-(2-pyrimidin-2-ylpyrimidin-5-yl)-3,4-dihydro-1H-isoquinoline (8 mg, 27.6 μmol, 2.18% yield) as white solid. $^1$H NMR (400 MHz, CDCl$_3$) δ ppm: 3.04-3.15 (m, 2H), 3.71-3.79 (m, 2H), 4.58-4.65 (m, 2H), 7.22-7.30 (m, 4H), 7.32-7.37 (m, 1H), 8.62 (s, 2H), 8.94-9.01 (m, 2H). MS obsd. (ESI$^+$) [(M+H)$^+$]: 290.

Example 2

7-Fluoro-2-(2-pyrimidin-2-ylpyrimidin-5-yl)-3,4-dihydro-1H-isoquinoline

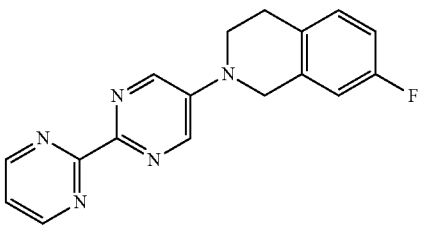 [SMILES: Fc1ccc2c(c1)CN(c1cnc(-c3ncccn3)nc1)CC2]

A mixture of 5-bromo-2-pyrimidin-2-yl-pyrimidine (200 mg, 844 μmol, the product of step 3 in Example 1), 7-fluoro-1,2,3,4-tetrahydroisoquinoline hydrochloride (190 mg, 1.01 mmol), sodium tert-butoxide (243 mg, 2.53 mmol), Ruphos (15.7 mg, 33.7 μmol) and Pd$_2$(dba)$_3$ (15.5 mg, 16.9 μmol) was heated at 100° C. with stirring for 3 hrs under N$_2$. The resulting mixture was cooled down to rt, then diluted with saturated aqueous NH$_4$Cl solution and extracted with DCM (40 mL) for three times. The combined organic layer was dried and concentrated in vacuo. The residue was purified by prep-HPLC to give 7-fluoro-2-(2-pyrimidin-2-ylpyrimidin-5-yl)-3,4-dihydro-1H-isoquinoline (15 mg) as light yellow solid. $^1$H NMR (400 MHz, Methanol-d$_4$) δ ppm: 2.98-3.07 (m, 2H), 3.73-3.80 (m, 2H), 4.63 (s, 2H), 6.92-7.01 (m, 1H), 7.02-7.10 (m, 1H), 7.19-7.27 (m, 1H), 7.46-7.59 (m, 1H), 8.56-8.71 (m, 2H), 8.95 (br. s., 2H). MS obsd. (ESI$^+$) [(M+H)$^+$]: 308.

Example 3

6,7-Dimethoxy-2-(2-pyrimidin-2-ylpyrimidin-5-yl)-3,4-dihydro-1H-isoquinoline

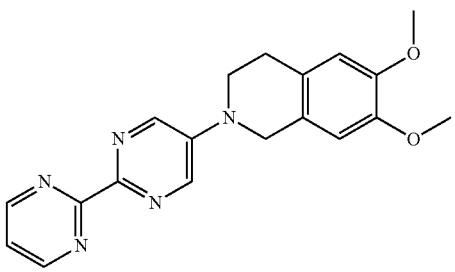

A mixture of 5-bromo-2-pyrimidin-2-yl-pyrimidine (105 mg, 443 μmol, the product of step 3 in Example 1), 6,7-dimethoxy-1,2,3,4-tetrahydroisoquinoline hydrochloride (102 mg, 443 μmol), sodium tert-butoxide (128 mg, 1.33 mmol), Pd$_2$(dba)$_3$ (8.11 mg, 8.86 μmol) and Ruphos (8.27 mg, 17.7 μmol) in toluene (10 mL) was heated at 100° C. under N$_2$ for 3 hrs. The resulting mixture was cooled to rt, diluted with saturated NH$_4$Cl and extracted with DCM (50 mL) for three times. The combined organic layer was dried over Na$_2$SO$_4$ and concentrated in vacuo. The residue was purified by prep-HPLC to give 6,7-dimethoxy-2-(2-pyrimidin-2-yl-pyrimidin-5-yl)-3,4-dihydro-1H-isoquinoline (3 mg) as light yellow solid. $^1$H NMR (400 MHz, CDCl$_3$) δ ppm: 2.93-3.07 (m, 2H), 3.67-3.79 (m, 2H), 3.91 (d, 6H), 4.45-4.60 (m, 2H), 6.73 (d, 2H), 7.32-7.41 (m, 1H), 8.54-8.70 (m, 2H), 8.88-9.04 (m, 2H). MS obsd. (ESI$^+$) [(M+H)$^+$]: 350.

Example 4

6-Methoxy-2-(2-pyrimidin-2-ylpyrimidin-5-yl)-3,4-dihydro-1H-isoquinoline

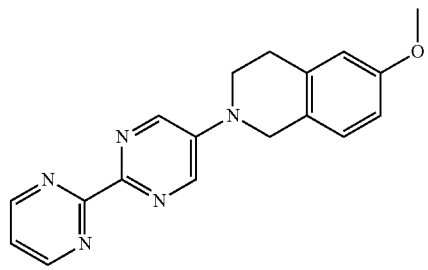 [SMILES: COc1ccc2c(c1)CCN(c1cnc(-c3ncccn3)nc1)C2]

A mixture of 5-bromo-2-pyrimidin-2-yl-pyrimidine (100 mg, 422 μmol, the product of step 3 in Example 1), 6-methoxy-1,2,3,4-tetrahydroisoquinoline hydrochloride (84.2 mg, 422 μmol), Pd$_2$(dba)$_3$ (386 mg, 422 μmol), Ruphos (197 mg, 422 μmol) and sodium tert-butoxide (40.5 mg, 422 μmol) in toluene (5 mL) was heated at 100° C. with stirring for 2 hrs under N$_2$. The reaction mixture was diluted with H$_2$O and extracted with EA (30 mL) for three times. The combined organic layer was dried over Na$_2$SO$_4$ and concentrated in vacuo. The residue was purified by pre-HPLC to give 6-methoxy-2-(2-pyrimidin-2-ylpyrimidin-5-yl)-3,4-dihydro-1H-isoquinoline (3 mg) as light yellow solid. $^1$H NMR (400 MHz, CDCl$_3$) δ ppm: 3.05 (t, 2H), 3.52 (s, 2H), 3.73 (t, 2H), 3.82-3.86 (m, 3H), 4.55 (s, 2H), 6.78 (d, 1H), 6.84 (dd, 1H), 7.18 (d, 1H), 7.35 (br. s., 1H), 8.51-8.68 (m, 2H), 8.92-9.05 (m, 2H).

Example 5

5-Fluoro-7-methoxy-2-(2-pyrimidin-2-ylpyrimidin-5-yl)-3,4-dihydro-1H-isoquinoline

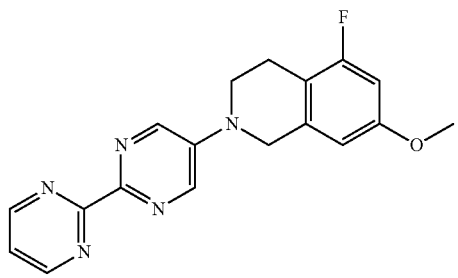 [SMILES: COc1cc(F)c2c(c1)CN(c1cnc(-c3ncccn3)nc1)CC2]

Step 1: N-[(3-fluoro-5-methoxy-phenyl)methyl]-2,2-dimethoxy-ethanamine

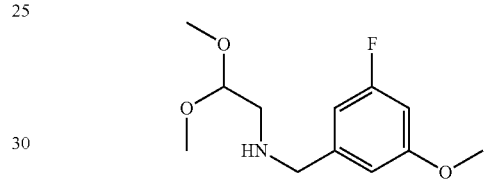

To a solution of 3-fluoro-5-methoxybenzaldehyde (25.0 g, 162.19 mmol) in toluene (250 mL) was added aminoacetaldehyde dimethyl acetal (18.8 g, 178.41 mmol). After being stirred at 120° C. for 8 hrs, the resulting mixture was concentrated in vacuo and the residue was dissolved in MeOH (300 mL). To the resulting solution was added NaBH$_4$ (7.1 g, 186.52 mmol) at 0° C. and the resulting mixture was warmed to rt and stirred for 30 mins, then quenched with H$_2$O (100 mL) and extracted with EA (100 mL) for three times. The combined organic phase was washed with brine, dried over anhydrous Na$_2$SO$_4$ and concentration in vacuo to give N-[(3-fluoro-5-methoxy-phenyl)methyl]-2,2-dimethoxy-ethanamine (30.0 g, crude) which was used directly in the next step without any further purification.

Step 2: Preparation of 5-fluoro-7-methoxy-1,2,3,4-tetrahydroisoquinolin-4-ol and 7-fluoro-5-methoxy-1,2,3,4-tetrahydroisoquinolin-4-ol

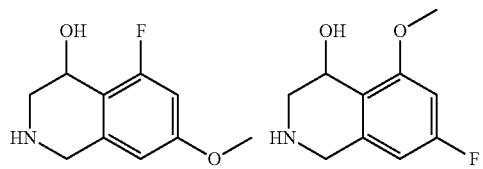

A mixture of N-[(3-fluoro-5-methoxy-phenyl)methyl]-2,2-dimethoxy-ethanamine (30.0 g, crude) and HCl (320 mL, 6N) was stirred at 40° C. for 12 hrs. The mixture was concentrated under reduced pressure to give a mixture of 5-fluoro-7-methoxy-1,2,3,4-tetrahydroisoquinolin-4-ol and 7-fluoro-5-methoxy-1,2,3,4-tetrahydroisoquinolin-4-ol (30.0 g, crude) which was used in the next step directly without any further purification.

Step 3: Preparation of 5-fluoro-7-methoxy-1,2,3,4-tetrahydroisoquinoline and 7-fluoro-5-methoxy-1,2,3,4-tetrahydroisoquinoline

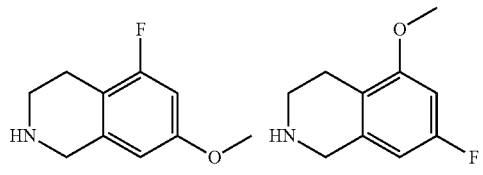

To a solution of 5-fluoro-7-methoxy-1,2,3,4-tetrahydroisoquinolin-4-ol and 7-fluoro-5-methoxy-1,2,3,4-tetrahydroisoquinolin-4-ol (30.0 g, crude) in DCM (210 mL) was added triethylsilane (35.4 g, 304.24 mmol) and TFA (90 mL). The resulting mixture was stirred at rt for 12 hrs and then concentrated in vacuo to give a mixture of 5-fluoro-7-methoxy-1,2,3,4-tetrahydroisoquinoline and 7-fluoro-5-methoxy-1,2,3,4-tetrahydroisoquinoline (25.0 g, crude) which was used in the next step directly without any further purification.

Step 4: Preparation of tert-butyl 5-fluoro-7-methoxy-3,4-dihydro-1H-isoquinoline-2-carboxylate and tert-butyl 7-fluoro-5-methoxy-3,4-dihydro-1H-isoquinoline-2-carboxylate

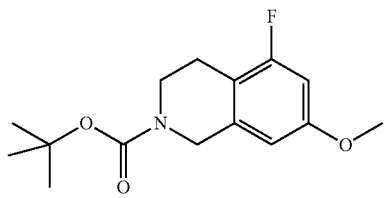

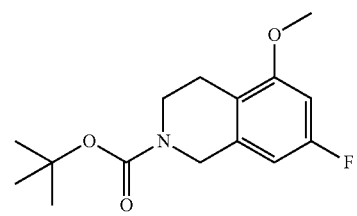

To a mixture of 5-fluoro-7-methoxy-1,2,3,4-tetrahydroisoquinoline and 7-fluoro-5-methoxy-1,2,3,4-tetrahydroisoquinoline (crude 25.0 g) in DCM (300 mL) was added TEA (115 mL, 827.77 mmol) and Boc$_2$O (43.4 g, 198.66 mmol). The mixture was stirred at rt for 12 hrs and concentrated in vacuo. The residue was diluted with EA (300 mL) and washed with brine. The organic layer was separated, then dried over anhydrous Na$_2$SO$_4$ and concentrated in vacuo. The residue was purified by flash column (eluting 2% EA in PE, v:v) to give tert-butyl 7-fluoro-5-methoxy-3,4-dihydro-1H-isoquinoline-2-carboxylate (8.34 g) and tert-butyl 5-fluoro-7-methoxy-3,4-dihydro-1H-isoquinoline-2-carboxylate (7.29 g) as a colorless oil.

Step 5: Preparation of 5-fluoro-7-methoxy-1,2,3,4-tetrahydroisoquinoline

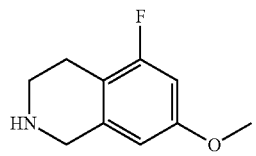

A mixture of tert-butyl 5-fluoro-7-methoxy-3,4-dihydro-1H-isoquinoline-2-carboxylate (7 g) and a solution of HCl in MeOH (4N, 50 mL) was stirred at rt overnight. The mixture was concentrated in vacuo and the residue was neutralized with saturated aqueous NaHCO3 solution. The resulting mixture was extracted with EA (50 mL) for three times. The combined organic layer was dried over anhydrous Na$_2$SO$_4$ and concentrated in vacuo to give 5-fluoro-7-methoxy-1,2,3,4-tetrahydroisoquinoline (4.5 g) as yellow oil, which was used in the next step without any further purification.

Step 6: Preparation of 5-fluoro-7-methoxy-2-(2-pyrimidin-2-ylpyrimidin-5-yl)-3,4-dihydro-1H-isoquinoline

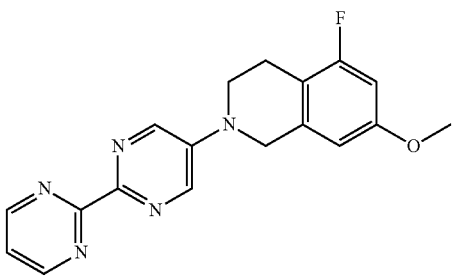 [SMILES: COc1cc(F)c2c(c1)CN(c1cnc(-c3ncccn3)nc1)CC2]

To a mixture of 5-bromo-2-pyrimidin-2-yl-pyrimidine (5.0 g, 27.59 mmol, the product of step 3 in Example 1), 5-fluoro-7-methoxy-1,2,3,4-tetrahydroisoquinoline (7.8 g, 33.11 mmol) and Cs$_2$CO$_3$ (36.0 g, 110.37 mmol) in 1,4-dioxane (60 mL) was added Ruphos (1.2 g), Pd$_2$(dba)$_3$ (1.2 g). The mixture was stirred under N$_2$ at 120° C. for 16 hrs. After being cooled to rt and filtered, the filtrate was concentrated in vacuo. The residue was purified by prep-HPLC to give 5-fluoro-7-methoxy-2-(2-pyrimidin-2-ylpyrimidin-5-yl)-3,4-dihydro-1H-isoquinoline (2.19 g) as yellow solid. $^1$H NMR (400 MHz, CDCl$_3$) δ ppm: 8.97 (d, 2H), 8.62 (s, 2H), 7.35 (t, 1H), 6.88 (s, 1H), 6.77 (d, 1H), 4.53 (s, 2H), 3.86 (s, 3H), 3.73 (t, 2H), 2.93 (t, 2H), MS obsd. (ESI$^+$) [(M+H)$^+$]: 338.

Example 6

7-Fluoro-5-methoxy-2-(2-pyrimidin-2-ylpyrimidin-5-yl)-3,4-dihydro-1H-isoquinoline

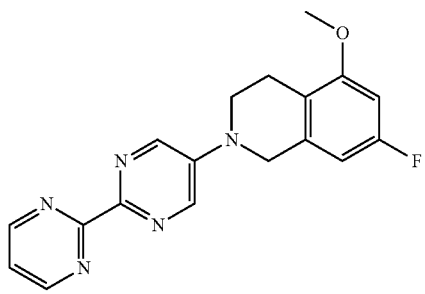 [SMILES: COc1cc(F)cc2c1CCN(c1cnc(-c3ncccn3)nc1)C2]

Step 1: Preparation of 7-fluoro-5-methoxy-1,2,3,4-tetrahydroisoquinoline

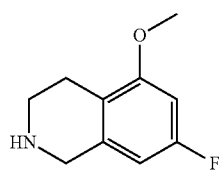

A mixture of tert-butyl 7-fluoro-5-methoxy-3,4-dihydro-1H-isoquinoline-2-carboxylate (1.0 g, 3.5 mmol) and a solution of HCl in EA (1N, 10 mL) was stirred at rt for 4 hrs. The mixture was concentrated in vacuo to afford 7-fluoro-5-methoxy-2-(2-pyrimidin-2-ylpyrimidin-5-yl)-3,4-dihydro-1H-isoquinoline hydrochloride (0.9 g, crude) a yellow solid which was used in the next step directly without any further purification.

Step 2: Preparation of 7-fluoro-5-methoxy-2-(2-pyrimidin-2-ylpyrimidin-5-yl)-3,4-dihydro-1H-isoquinoline

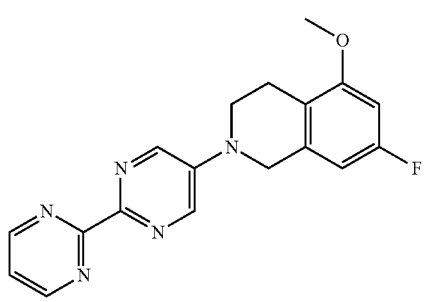 [SMILES: COc1cc(F)cc2c1CCN(c1cnc(-c3ncccn3)nc1)C2]

To a solution of 7-fluoro-5-methoxy-2-(2-pyrimidin-2-ylpyrimidin-5-yl)-3,4-dihydro-1H-isoquinoline hydrochloride (150 mg, 0.70 mmol) in dioxane (10 mL) was added 5-bromo-2-pyrimidin-2-yl-pyrimidine (170 mg, 0.75 mmol, the product of step 3 in Example 1), followed by Pd$_2$(dba)$_3$ (13 mg, 0.014 mmol), Ruphos (16 mg, 0.035 mmol) and tert-BuONa (168 mg, 1.75 mmol). After being stirred at 100° C. for 12 hrs under N$_2$ and cooled to rt, the resulting reaction mixture was diluted with EA (30 mL) and filtered. The filtrate was washed with H$_2$O (10 mL). The organic layer was dried over anhydrous Na$_2$SO$_4$, filtered and concentrated in vacuo. The residue was purified by prep-HPLC to give 7-fluoro-5-methoxy-2-(2-pyrimidin-2-ylpyrimidin-5-yl)-3,4-dihydro-1H-isoquinoline (5 mg, yield: 2.1%) as a yellow solid. $^1$H NMR (400 MHz, CDCl$_3$) δ ppm: 8.88 (d, 2H), 8.53 (s, 2H), 7.12-7.36 (m, 2H), 6.32-6.60 (m, 2H), 4.45 (br. s., 2H), 3.76 (s, 3H), 3.64 (br. s., 2H), 2.83 (br. s., 2H). MS obsd. (ESI$^+$) [(M+H)$^3$]: 338.

Example 7

5-Fluoro-7-methoxy-1-methyl-2-(2-pyrimidin-2-ylpyrimidin-5-yl)-3,4-dihydro-1H-isoquinoline

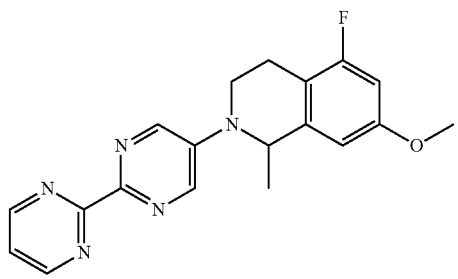

Step 1: Preparation of 5-fluoro-1,7-dimethoxy-2-(2-pyrimidin-2-ylpyrimidin-5-yl)-3,4-dihydro-1H-isoquinoline

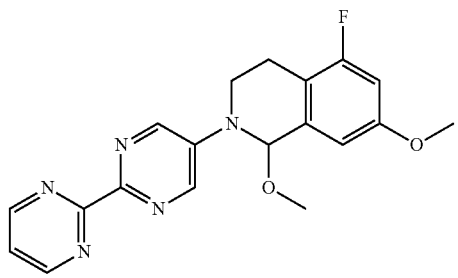 [SMILES: COc1cc(F)c2c(c1)C(OC)N(c1cnc(-c3ncccn3)nc1)CC2]

To a solution of 5-fluoro-7-methoxy-2-(2-pyrimidin-2-ylpyrimidin-5-yl)-3,4-dihydro-1H-isoquinoline (78 mg, 0.15 mmol, Example 5) in THF (1 mL) and MeOH (4 mL), which was cooled to −40° C., was added RuCl$_3$ hydrate (3 mg, 0.01 mmol) and a solution of NaIO$_4$ (97 mg, 0.45 mmol) in H$_2$O (2 mL) slowly. The resulting mixture was stirred for 15 min at −40° C., and then warmed rt and stirred for 4 hrs. The resulting reaction mixture was then diluted with saturated aqueous Na$_2$SO$_3$ (10 mL) and extracted with DCM (20 mL) twice. The combined organic layer was washed with H$_2$O (10 mL) and the organic layer was dried over anhydrous Na$_2$SO$_4$, filtered and concentrated in vacuo to give 5-fluoro-1,7-dimethoxy-2-(2-pyrimidin-2-ylpyrimidin-5-yl)-3,4-dihydro-1H-isoquinoline (50 mg, crude) as a black oil, which was used in the next step directly without any further purification.

Step 2: Preparation of 5-fluoro-7-methoxy-1-methyl-2-(2-pyrimidin-2-ylpyrimidin-5-yl)-3,4-dihydro-1H-isoquinoline

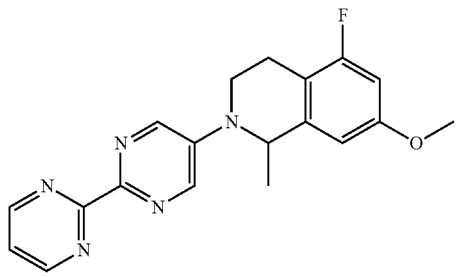

To a stirred solution of 5-fluoro-1,7-dimethoxy-2-(2-pyrimidin-2-ylpyrimidin-5-yl)-3,4-dihydro-1H-isoquinoline (50 mg, 0.136 mmol) in THF (1 mL), which was cooled to −40° C., was added BF$_3$·Et$_2$O (47 mg, 0.408 mmol) and MeMgBr (0.14 mL, 0.408 mmol) successively. The resulting mixture was warmed to 0° C. and stirred for 1 hr, then diluted with saturated aqueous NH$_4$Cl (50 mL) and extracted with (20 mL) for three times. The combined organic layer was dried over anhydrous Na$_2$SO$_4$, filtered and concentrated in vacuo. The residue was purified by prep-HPLC to give 5-fluoro-7-methoxy-1-methyl-2-(2-pyrimidin-2-ylpyrimidin-5-yl)-3,4-dihydro-1H-isoquinoline (2.4 mg) as light yellow solid. $^1$H NMR (400 MHz, CDCl$_3$) δ ppm: 8.97 (d, 1H), 8.60 (s, 1H), 7.34 (t, 1H), 6.54-6.62 (m, 2H), 5.00 (q, 1H), 3.79-3.90 (m, 4H), 3.62 (ddd, 1H), 2.86-3.10 (m, 1H), 1.58 (d, 3H). MS obsd. (ESI$^+$) [(M+H)$^+$]: 352.

Example 8

5-Fluoro-7-methoxy-2-(5-pyrimidin-2-ylpyrazin-2-yl)-3,4-dihydro-1H-isoquinoline

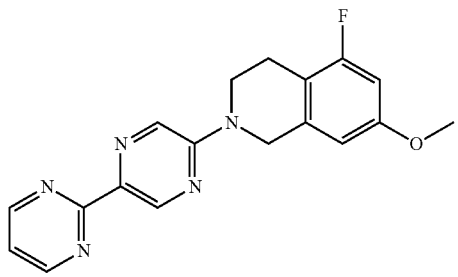

Step 1: Preparation of 2-(5-chloropyrazin-2-yl)-5-fluoro-7-methoxy-3,4-dihydro-1H-isoquinoline

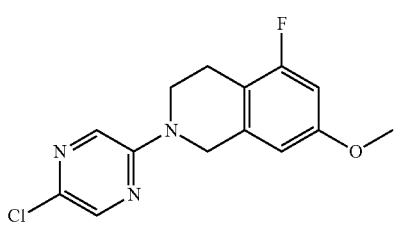 [SMILES: COc1cc(F)c2c(c1)CN(c1cnc(Cl)cn1)CC2]

To a stirring solution of 5-fluoro-7-methoxy-1,2,3,4-tetrahydroisoquinoline (100 mg, 0.55 mmol) in DMSO (1 mL) was added 2,5-dichloropyrazine (160 mg, 1.1 mmol) and DIPEA (170 mg, 1.65 mmol). The mixture was stirred at 100° C. for 4 hrs and then diluted with EA (100 mL). The resulting mixture was washed with H$_2$O (40 mL) and brine (40 mL) successively, dried over anhydrous Na$_2$SO$_4$ and concentrated in vacuo. The residue was purified by flash column (eluting with PE:EA=10:1, v:v) to get 2-(5-chloropyrazin-2-yl)-5-fluoro-7-methoxy-3,4-dihydro-1H-isoquinoline (100 mg) as white solid.

Step 2: Preparation of 5-fluoro-7-methoxy-2-(5-pyrimidin-2-ylpyrazin-2-yl)-3,4-dihydro-1H-isoquinoline

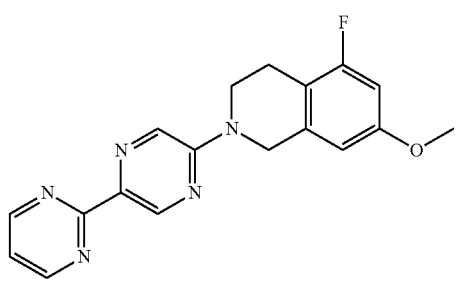

A mixture of 2-(5-chloropyrazin-2-yl)-5-fluoro-7-methoxy-3,4-dihydro-1H-isoquinoline (80 mg, 0.272 mmol), 2-(tributylstannyl)pyrimidine (302 mg, 0.817 mmol) and cataCXium® A Pd G2 (18.2 mg, 0.027 mmol, Vendor: Sigma-Aldrich, CAS: 1375477-29-4) in EtOH (2 mL) was heated at 80° C. under nitrogen for 12 hrs. The resulting reaction mixture was diluted with DCM (80 mL) and washed with brine (20 mL). The organic phase was concentrated in vacuo and the residue was purified by prep-HPLC to afford 5-fluoro-7-methoxy-2-(5-pyrimidin-2-ylpyrazin-2-yl)-3,4-dihydro-1H-isoquinoline (15 mg) as a white solid. $^1$H NMR (400 MHz, CDCl$_3$) δ ppm: 9.27 (d, 1H), 8.84 (d, 2H), 8.34 (d, 1H), 7.21 (t, 1H), 6.61 (s, 1H), 6.56 (dd, 1H), 4.85 (s, 2H), 3.99 (t, 2H), 3.81 (s, 3H), 2.94 (t, 2H). MS obsd. (ESI$^+$) [(M+H)$^+$]: 338.

Example 9

6-Chloro-2-(2-pyrimidin-2-ylpyrimidin-5-yl)-3,4-dihydro-1H-isoquinoline

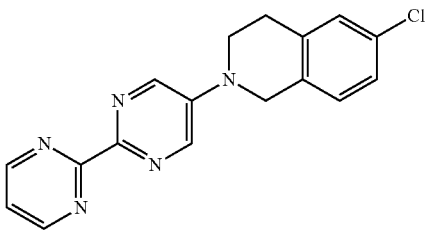 [SMILES: Clc1ccc2c(c1)CCN(c1cnc(-c3ncccn3)nc1)C2]

Step 1: Preparation of N-[(3-chlorophenyl)methyl]formamide

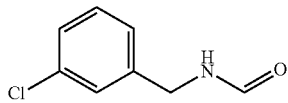 [SMILES: O=CNCc1cccc(Cl)c1]

A mixture of 2-(3-chlorophenyl)ethanamine (2.3 g, 14.8 mmol) and formic acid (680 mg, 567 μl, 14.8 mmol) was heated with stirring at 100° C. overnight. The resulting mixture was cooled to rt and concentrated in vacuo. The residue was purified by column (eluting with PE:EA=2:1, v:v) to give N-(3-chlorophenethyl)formamide (2.3 g, 12.5 mmol) as light yellow oil.

Step 2: Preparation of 8-chloro-6,10b-dihydro-5H-oxazolo[2,3-a]isoquinoline-2,3-dione

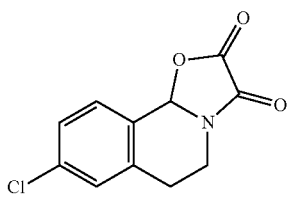 [SMILES: O=C1OC2c3ccc(Cl)cc3CCN2C1=O]

To a solution of N-(3-chlorophenethyl)formamide (0.9 g, 4.9 mmol) in DCM (15 mL) was added oxalyl chloride (684 mg, 472 μL, 5.39 mmol). The mixture was stirred at rt for 30 mins and then cooled to 0° C. To the cooled mixture was added iron (III) chloride (954 mg, 5.88 mmol). The resulting mixture was then warmed to rt and stirred overnight. The resulting reaction mixture was then treated with 1N HCl (50 mL) and extracted with DCM (50 mL) twice. The combined organic layer was dried over anhydrous $Na_2SO_4$ and concentrated in vacuo to give crude 8-chloro-6,10b-dihydro-5H-oxazolo[2,3-a]isoquinoline-2,3-dione (1.3 g) as brown oil which was used in the next step directly without any further purification.

Step 3: Preparation of 6-chloro-3,4-dihydroisoquinoline

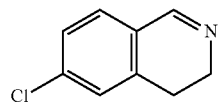 [SMILES: Clc1ccc2c(c1)CCN=C2]

A mixture of 8-chloro-6,10b-dihydro-5H-oxazolo[2,3-a]isoquinoline-2,3-dione (1.29 g, 5.43 mmol) and a solution of 10% $H_2SO_4$ in MeOH (2 mL in 20 mL MeOH) was heated at 80° C. for 2 hrs. The resulting mixture then was concentrated in vacuo. The residue was diluted with saturated aqueous $NaHCO_3$ solution and extracted with DCM (30 mL) for three times. The combined DCM layer was dried over anhydrous $Na_2SO_4$ and concentrated in vacuo. The residue was purified by column (eluting with DCM:MeOH=20:1, v:v) to 6-chloro-3,4-dihydroisoquinoline (400 mg) as yellow oil.

Step 4: Preparation of 6-chloro-1,2,3,4-tetrahydroisoquinoline

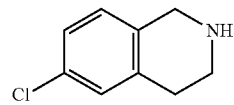 [SMILES: Clc1ccc2c(c1)CCNC2]

To a solution of 6-chloro-3,4-dihydroisoquinoline (400 mg, 2.42 mmol) in EtOH (20 mL) was added sodium borohydride (228 mg, 6.04 mmol). After being stirred at rt for 1 hr, the reaction was quenched with 1N HCl. The resulting mixture was extracted with EA (30 mL) for three times. The combined EA layer was dried over anhydrous $Na_2SO_4$ and concentrated in vacuo to give crude 6-chloro-1,2,3,4-tetrahydroisoquinoline (150 mg) as grey solid which was used in the next step directly without any further purification.

Step 5: Preparation of 6-chloro-2-(2-pyrimidin-2-ylpyrimidin-5-yl)-3,4-dihydro-1H-isoquinoline

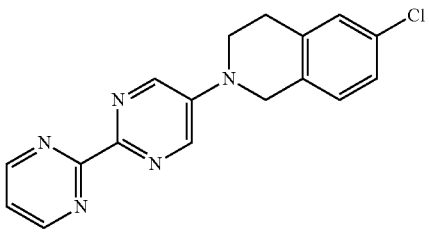 [SMILES: Clc1ccc2c(c1)CCN(c1cnc(-c3ncccn3)nc1)C2]

A mixture of 5-bromo-2-pyrimidin-2-yl-pyrimidine (150 mg, 633 μmol, the product of step 3 in Example 1), 6-chloro-1,2,3,4-tetrahydroisoquinoline (127 mg, 759 μmol), Ruphos (11.8 mg, 25.3 μmol), $Pd_2(dba)_3$ (11.6 mg, 12.7 μmol) and sodium tert-butoxide (122 mg, 1.27 mmol) in dioxane (10 mL) was heated at 110° C. with stirring overnight. After being cooled to rt, the resulting mixture was diluted with $H_2O$ and extracted with EA (50 mL) for three times. The combined EA layer was dried over anhydrous $Na_2SO_4$ and concentrated in vacuo. The residue was purified by prep-HPLC to give 6-chloro-2-(2-pyrimidin-2-ylpyrimidin-5-yl)-3,4-dihydro-1H-isoquinoline (10 mg) as light yellow solid. $^1$H NMR (400 MHz, $CDCl_3$) δ ppm: 2.99-3.08 (m, 2H), 3.72 (s, 2H), 4.55 (s, 2H), 7.15-7.20 (m, 1H), 7.23 (s, 2H), 7.31-7.36 (m, 1H), 8.60 (s, 2H), 8.96 (d, 2H). MS obsd. (ESI$^+$) [(M+H)$^+$]: 324.

Example 10

6,7-Dimethoxy-2-[6-(2-pyridyl)-3-pyridyl]-3,4-dihydro-1H-isoquinoline

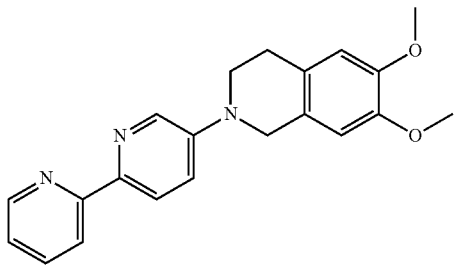 [SMILES: COc1cc2c(cc1OC)CN(c1ccc(-c3ccccn3)nc1)CC2]

A mixture of 6,7-dimethoxy-1,2,3,4-tetrahydroisoquinoline (136 mg, 702 μmol), 5-bromo-2-(2-pyridyl)pyridine (150 mg, 638 μmol, Vendor: J&K chemical, CAS registry number: 15862-19-8), Pd$_2$(dba)$_3$ (11.7 mg, 12.8 μmol), Ruphos (11.9 mg, 25.5 μmol) and sodium tert-butoxide (123 mg, 1.28 mmol) in dioxane (20 mL) was heated at 110° C. with stirring under N$_2$. The resulting mixture was cooled to rt, then diluted with H$_2$O (10 mL) and extracted with EA (20 mL) for three times. The combined EA layer was dried over anhydrous Na$_2$SO$_4$ and concentrated in vacuo. The residue was purified by prep-HPLC to give 6,7-dimethoxy-2-[6-(2-pyridyl)-3-pyridyl]-3,4-dihydro-1H-isoquinoline (22 mg) as yellow solid. $^1$H NMR (400 MHz, CDCl$_3$) δ ppm: 2.91-2.98 (m, 2H), 3.63-3.70 (m, 2H), 3.88 (d, 6H), 4.42-4.48 (m, 2H), 6.68 (d, 2H), 7.21-7.26 (m, 1H), 7.30-7.37 (m, 1H), 7.75-7.83 (m, 1H), 8.26 (d, 2H), 8.40-8.45 (m, 1H), 8.64 (d, 1H). MS obsd. (ESI$^+$) [(M+H)$^+$]: 348.

Example 11

7-Fluoro-2-(2-pyrimidin-2-ylpyrimidin-5-yl)-3,4-dihydro-1H-isoquinoline

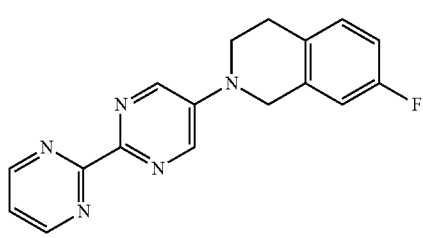 [SMILES: Fc1ccc2c(c1)CN(c1cnc(-c3ncccn3)nc1)CC2]

Step 1: Preparation of N-[(3-fluorophenyl)methyl]formamide

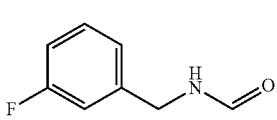 [SMILES: O=CNCc1cccc(F)c1]

A mixture of 2-(3-fluorophenyl)ethanamine (4 g, 28.7 mmol) and formic acid (1.98 g, 1.65 ml, 43.1 mmol) in dioxane (40 mL) was heated at 100° C. with stirring overnight. The resulting mixture was concentrated in vacuo and purified by column (eluting with PE/EA=5/1, v:v) to give N-(3-fluorophenethyl)formamide (4.1 g) as yellow oil.

Step 2: Preparation of 8-fluoro-6,10b-dihydro-5H-oxazolo[2,3-a]isoquinoline-2,3-dione

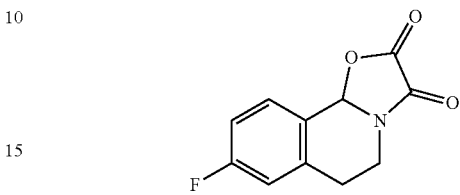

To a solution of N-(3-fluorophenethyl)formamide (2.05 g, 12.3 mmol) in DCM (40 mL) was added oxalyl chloride (1.71 g, 1.18 mL, 13.5 mmol). The mixture was stirred at rt for 30 min and then cooled to 0° C. To the mixture was added iron (III) chloride (2.39 g, 14.7 mmol) and the resulting reaction mixture was stirred at rt for 3 hrs. Then the reaction was quenched with 3N HCl and the resulting mixture was extracted with EA (50 mL) for three times. The combined EA layer was dried over anhydrous Na$_2$SO$_4$ and concentrated in vacuo to give crude 8-fluoro-6,10b-dihydro-5H-oxazolo[2,3-a]isoquinoline-2,3-dione (2.8 g) as yellow solid, which was used in the next step without any further purification.

Step 3: Preparation of 6-fluoro-3,4-dihydroisoquinoline

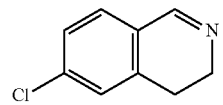 [SMILES: Clc1ccc2c(c1)CCN=C2]

To a solution of 8-fluoro-6,10b-dihydro-5H-oxazolo[2,3-a]isoquinoline-2,3-dione (2.8 g, 12.7 mmol) in MeOH (40 mL) was added sulfuric acid (4 mL). The resulting mixture was heated at 90° C. with stirring for 2 hrs, and concentrated in vacuo. The residue was diluted with saturated aqueous NaHCO$_3$ solution and extracted with EA (50 mL) for 3 times. The combined organic layer was dried over anhydrous Na$_2$SO$_4$ and concentrated in vacuo to give crude 6-fluoro-3,4-dihydroisoquinoline which was used in the next step directly without any further purification.

Step 4: Preparation of 6-fluoro-1,2,3,4-tetrahydroisoquinoline

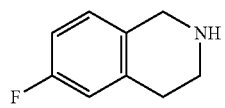

To a solution of 6-fluoro-3,4-dihydroisoquinoline (1.9 g, 12.7 mmol) in MeOH (30 mL) was added sodium borohydride (482 mg, 12.7 mmol). After being stirred for 10 mins, the resulting mixture was concentrated in vacuo and the residue was purified by column (eluting with PE/EA=2/1, v:v) to give 6-fluoro-1,2,3,4-tetrahydroisoquinoline (500 mg) as yellow oil.

Step 5: Preparation of 7-fluoro-2-(2-pyrimidin-2-ylpyrimidin-5-yl)-3,4-dihydro-1H-isoquinoline

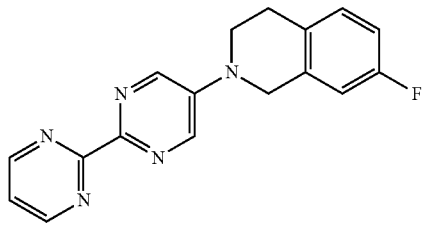 [SMILES: Fc1ccc2c(c1)CN(c1cnc(-c3ncccn3)nc1)CC2]

A mixture of 6-fluoro-1,2,3,4-tetrahydroisoquinoline (191 mg, 1.27 mmol), 5-bromo-2-pyrimidin-2-yl-pyrimidine (250 mg, 1.05 mmol, the product of step 3 in Example 1), Pd$_2$(dba)$_3$ (19.3 mg, 21.1 μmol), Ruphos (19.7 mg, 42.2 μmol) and sodium tert-butoxide (203 mg, 2.11 mmol) in dioxane (20 mL) was heated at 100° C. with stirring overnight. The resulting mixture was diluted H$_2$O (20 mL) and extracted with DCM (20 mL) for three times. The combined organic layer was concentrated in vacuo and the residue was purified by prep-HPLC to give 7-fluoro-2-(2-pyrimidin-2-ylpyrimidin-5-yl)-3,4-dihydro-1H-isoquinoline (10 mg) as light yellow solid. $^1$H NMR (400 MHz, CDCl$_3$) δ ppm: 3.05 (t, 2H), 3.72 (s, 2H), 4.55 (s, 2H), 6.89-7.03 (m, 2H), 7.18-7.23 (m, 1H), 7.31-7.36 (m, 1H), 8.49-8.69 (m, 2H), 8.87-9.05 (m, 2H). MS obsd. (ESI$^+$) [(M+H)$^+$]:308.

Example 12

2-Methoxy-7-(2-pyrimidin-2-ylpyrimidin-5-yl)-6,8-dihydro-5H-1,7-naphthyridine

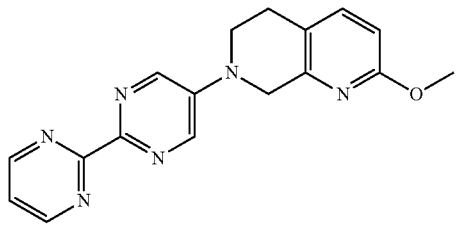 [SMILES: COc1ccc2c(n1)CN(c1cnc(-c3ncccn3)nc1)CC2]

Step 1: Preparation of ethyl (E)-3-(3-amino-4-pyridyl)prop-2-enoate

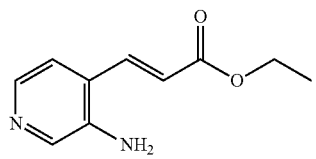

A mixture of 3-amino-4-bromopyridine (5.0 g, 28.9 mmol), (E)-ethyl 3-(4,4,5,5-tetramethyl-1,3,2-dioxaborolan-2-yl) acrylate (7.84 g, 34.7 mmol), Pd(OAc)$_2$ (250 mg), Xantphos (400 mg) and K$_2$CO$_3$ (5.18 g, 37.6 mmol) in THF (150 mL) and H$_2$O (30 mL) was stirred at 80° C. for 16 hrs. The resulting mixture was filtered. The filtrate was diluted with EA (100 mL), washed with brine (100 mL), then dried over Na$_2$SO$_4$ and concentrated in vacuo. The residue was purified by column (PE:EA=10:1 to DCM:MeOH=50:1, v:v) to give ethyl (E)-3-(3-amino-4-pyridyl)prop-2-enoate (3.1 g) as a brown solid.

Step 2: Preparation of 1H-1,7-naphthyridin-2-one

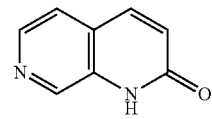

To EtOH was added metal Na (1.25 g, 54.2 mmol) in portions (60 mL) at rt and stirred until Na was fully dissolved. To the resulting solution was added a solution of ethyl (E)-3-(3-amino-4-pyridyl)prop-2-enoate (2.6 g, 13.5 mmol) in EtOH (15 mL). The resulting mixture was stirred at 90° C. for 1 hr and then concentrated in vacuo. The residue was purified by column (eluting with DCM: MeOH=10:1, v:v) to give 1H-1,7-naphthyridin-2-one (1.6 g) as a yellow solid.

Step 3: Preparation of 7-benzyl-1,5,6,8-tetrahydro-1,7-naphthyridin-2-one

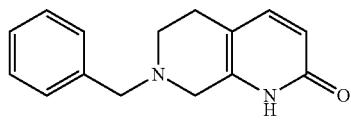 [SMILES: O=c1ccc2c([nH]1)CN(Cc1ccccc1)CC2]

To a solution of 1H-1,7-naphthyridin-2-one (1.6 g, 11.0 mmol) in MeOH (50 mL) was added BnBr (2.1 g, 12.1 mmol) at to 70° C. The resulting mixture was stirred at 70° C. for 3 hrs and then cooled to 0° C. To the cooled mixture was added NaBH$_4$ (2.09 g, 55.0 mmol). The resulting mixture was slowly warmed to rt and stirred for 3 hrs at rt. The reaction was quenched with 6N HCl (20 mL). The resulting mixture was stirred at rt for 2 hrs, then basified with 2 N NaOH to pH 10 and extracted with DCM (50 mL) twice. The combined organic layer was dried over Na$_2$SO$_4$ and concentrated in vacuo. The residue was purified by column (eluting with DCM:MeOH=40:1, v:v) to give 7-benzyl-1,5,6,8-tetrahydro-1,7-naphthyridin-2-one (700 mg) as a yellow solid.

Step 4: Preparation of tert-butyl 2-oxo-1,5,6,8-tetrahydro-1,7-naphthyridine-7-carboxylate

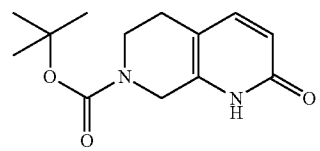 [SMILES: CC(C)(C)OC(=O)N1CCc2ccc(=O)[nH]c2C1]

A mixture of 7-benzyl-1,5,6,8-tetrahydro-1,7-naphthyridin-2-one (700 mg, 2.92 mmol), Boc₂O (954 mg, 4.37 mmol) in MeOH (20 mL) and DCM (5 mL) was hydrogenated in the presence of Pd/C (70 mg) at rt under H₂ (balloon) for 16 hrs. The resulting mixture was filtered and the filtrate was concentrated in vacuo. The residue was purified by column (eluting with DCM:MeOH=30:1, v:v) to give tert-butyl 2-oxo-1,5,6,8-tetrahydro-1,7-naphthyridine-7-carboxylate (500 mg) as a yellow oil.

Step 5: Preparation of tert-butyl 2-methoxy-6,8-dihydro-5H-1,7-naphthyridine-7-carboxylate

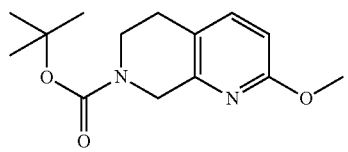 [SMILES: COc1ccc2c(n1)CN(C(=O)OC(C)(C)C)CC2]

To a stirring solution of tert-butyl 2-oxo-1,5,6,8-tetrahydro-1,7-naphthyridine-7-carboxylate (390 mg, 1.56 mmol) in toluene (5 mL) was added Ag₂O (3.61 g, 15.6 mmol) and MeI (2.21 g, 15.6 mmol). The resulting mixture was stirred at rt for 12 hrs and filtered. The filtrate was concentrated in vacuo and the residue was purified by prep-TLC (developing with DCM:MeOH=10:1, v:v) to afford tert-butyl 2-methoxy-6,8-dihydro-5H-1,7-naphthyridine-7-carboxylate (400 mg, crude) as colorless oil.

Step 6: Preparation of 2-methoxy-5,6,7,8-tetrahydro-1,7-naphthyridine

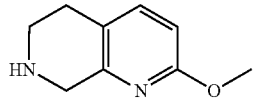

A mixture of tert-butyl 2-methoxy-6,8-dihydro-5H-1,7-naphthyridine-7-carboxylate (400 mg, 1.51 mmol) and a solution of HCl in EA (2 mL, 1.0 M) was stirred at rt for 2 hrs. The resulting reaction mixture was concentrated in vacuo. The residue was dissolved in MeOH (3 mL), then stirred with basic resin (150 mg) at rt for 2 hrs and filtered. The filtrate was concentrated in vacuo to afford 2-methoxy-5,6,7,8-tetrahydro-1,7-naphthyridine (140 mg, crude) as a yellow solid, which was used in the next step without any further purification.

Step 7: Preparation of 2-methoxy-7-(2-pyrimidin-2-ylpyrimidin-5-yl)-6,8-dihydro-5H-1,7-naphthyridine

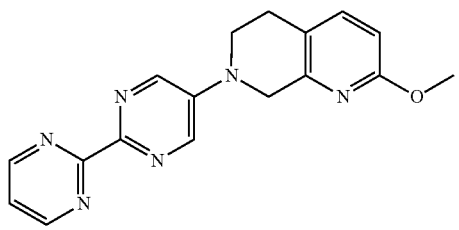 [SMILES: COc1ccc2c(n1)CN(c1cnc(-c3ncccn3)nc1)CC2]

To a solution of 2-methoxy-5,6,7,8-tetrahydro-1,7-naphthyridine (50 mg, 0.21 mmol) in t-amyl alcohol (1 mL) was added 5-bromo-2-pyrimidin-2-yl-pyrimidine (52 mg, 0.32 mmol, the product of step 3 in Example 1), followed by tert-BuXPhos Pd G3 (14 mg, 0.021 mmol, CAS registry number: 1447963-75-8), tert-BuOK (71 mg, 0.63 mmol). The resulting mixture was stirred at 110° C. for 12 hrs and then concentrated in vacuo. The residue was purified by prep-TLC (eluting with DCM:MeOH=10:1, v:v) and further purified by prep-HPLC to afford 2-methoxy-7-(2-pyrimidin-2-ylpyrimidin-5-yl)-6,8-dihydro-5H-1,7-naphthyridine (6.8 mg) as a white solid. ¹H NMR (400 MHz, Methanol-d₄) δ ppm: 8.95 (d, 2H), 8.70 (s, 2H), 7.46-7.58 (m, 2H), 6.66 (d, 1H), 4.57 (s, 2H), 3.91 (s, 3H), 3.82 (t, 2H), 2.96 (t, 2H). MS obsd. (ESI⁺) [(M+H)⁺]: 321.

Example 13

7-Methoxy-2-(2-pyrimidin-2-ylpyrimidin-5-yl)-3,4-dihydro-1H-2,6-naphthyridine

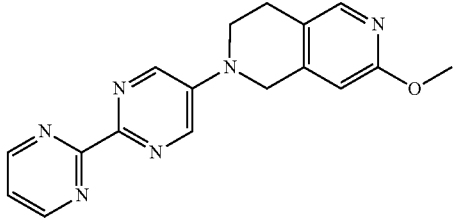 [SMILES: COc1cc2c(cn1)CCN(c1cnc(-c3ncccn3)nc1)C2]

Step 1: Preparation of 5-bromo-2-methoxy-pyridine-4-carbaldehyde

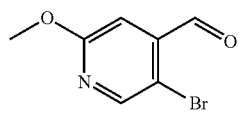

To a solution of i-Pr₂NH (13.4 g, 133.0 mmol) in THF (100 mL) at 0° C. was added n-BuLi (53 mL, 133.0 mmol, 2.5 M in hexane). The resulting mixture was stirred at 0° C. for 30 min and then was added to a solution of 5-bromo-2-methoxypyridine (20.0 g, 106.4 mmol) in THF (50 mL) at −78° C. The resulting mixture was stirred at −78° C. for 1 hr, then to the reaction mixture was added N,N-dimethylformamide (15.6 g, 212.7 mmol). The reaction mixture was warmed to 0° C. and then the reaction was quenched with saturated aqueous NH₄Cl. The resulting mixture was diluted with EA (600 mL), then washed with H₂O (200 mL) and brine (200 mL), dried over anhydrous Na₂SO₄ and concentrated in vacuo to afford 5-bromo-2-methoxy-pyridine-4-carbaldehyde (23.5 g, crude) as a yellow solid, which was used in the next step directly.

Step 2: Preparation of methyl 5-bromo-2-methoxy-pyridine-4-carboxylate

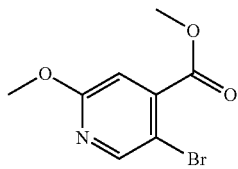

To a solution of 5-bromo-2-methoxy-pyridine-4-carbaldehyde (23.5 g, 108.8 mmol) in MeOH (100 mL) were successively added a solution of $I_2$ (35.9 mg, 141.4 mmol) in MeOH (75 mL) and a solution of KOH (15.9 g, 282.8 mmol) in MeOH (75 mL) at 0° C. The resulting mixture was stirred for 1 hr at 0° C. and the reaction was quenched with saturated aqueous $NaHSO_3$. The resulting mixture was diluted with DCM (400 mL). The separated organic phase was washed with $H_2O$ (150 mL) and brine (150 mL), dried over anhydrous $Na_2SO_4$ and concentrated in vacuo. The residue was purified by flash column (eluting with PE:EA=20:1, v:v) to give methyl 5-bromo-2-methoxy-pyridine-4-carboxylate (14.9 g) as a light yellow solid.

Step 3: Preparation of methyl 5-[(E)-2-(1,3-dioxoisoindolin-2-yl)vinyl]-2-methoxy-pyridine-4-carboxylate

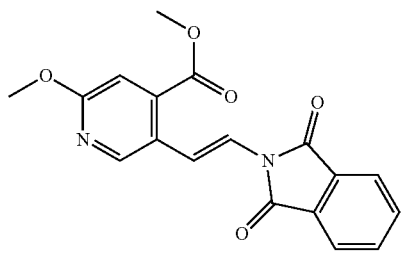 [SMILES: COC(=O)c1cc(OC)ncc1/C=C/N1C(=O)c2ccccc2C1=O]

To a solution of methyl 5-bromo-2-methoxy-pyridine-4-carboxylate (1.0 g, 4.1 mmol) and 2-vinylisoindoline-1,3-dione (844 mg, 4.88 mmol) in dioxane (32 mL) was added $Cy_2NMe$ (952 mg, 4.88 mmol) and tert-$Bu_3P$ Pd G2 (63 mg, 0.12 mmol, CAS registry number: 1375325-71-5). The reaction mixture was degassed with $N_2$ and heated at 90° C. for 12 hrs under $N_2$. The reaction mixture was concentrated in vacuo and the residue was purified by column gel (eluting with DCM) to give methyl 5-[(E)-2-(1,3-dioxoisoindolin-2-yl)vinyl]-2-methoxy-pyridine-4-carboxylate (1.3 g, crude) as a yellow solid.

Step 4: Preparation of methyl 5-[2-(1,3-dioxoisoindolin-2-yl)ethyl]-2-methoxy-pyridine-4-carboxylate

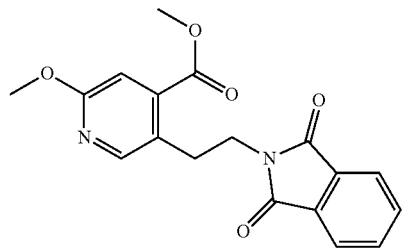 [SMILES: COC(=O)c1cc(OC)ncc1CCN1C(=O)c2ccccc2C1=O]

To a solution of methyl 5-[(E)-2-(1,3-dioxoisoindolin-2-yl)vinyl]-2-methoxy-pyridine-4-carboxylate (1.3 g, 3.84 mmol) in EtOH (30 mL) and THF (30 mL) was added Wilkinson's catalyst (711 mg, 0.77 mmol). The resulting mixture was hydrogenated on an H-Cube (2.4 MPa) and heated at 75° C. for 12 hrs. The resulting reaction mixture was concentrated in vacuo. The residue was purified by column gel (eluting with DCM) to give methyl 5-[2-(1,3-dioxoisoindolin-2-yl)ethyl]-2-methoxy-pyridine-4-carboxylate (1.2 g, crude) as a yellow oil.

Step 5: Preparation of 7-methoxy-3,4-dihydro-2H-2,6-naphthyridin-1-one

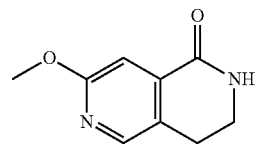

A mixture of methyl 5-[2-(1,3-dioxoisoindolin-2-yl)ethyl]-2-methoxy-pyridine-4-carboxylate (1.2 g, 3.53 mmol) and hydrazine hydrate (1.77 g, 35.3 mmol) in EtOH (10 mL) was heated at 70° C. for 5 hrs. The resulting reaction mixture was concentrated in vacuo. The residue was diluted with DCM (40 mL) and filtrated. The filtrate was concentrated in vacuo. The residue was purified by flash column (eluting with DCM:MeOH=20:1, v:v) to give 7-methoxy-3,4-dihydro-2H-2,6-naphthyridin-1-one (650 mg, crude) as a light yellow solid.

Step 6: Preparation of 7-methoxy-1,2,3,4-tetrahydro-2,6-naphthyridine

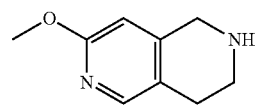

To a mixture of $LiAlH_4$ (255 mg, 6.73 mmol) and THF (5 mL) was added a solution of 7-methoxy-3,4-dihydro-2H-2,6-naphthyridin-1-one (300 mg, 1.68 mmol) in THF (5 mL) slowly at 0° C. Then the resulting mixture was warmed up to 20° C. and stirred for 5 hrs. The reaction was quenched with $H_2O$ (0.25 mL) and 15% NaOH (0.25 mL). The resulting mixture wad filtered and the filter cake was washed with DCM (20 mL). The filtrate was combined and concentrated in vacuo. The residue was purified by prep-HPLC to afford 7-methoxy-1,2,3,4-tetrahydro-2,6-naphthyridine (80 mg) as a yellow solid.

Step 7: Preparation of 7-methoxy-2-(2-pyrimidin-2-ylpyrimidin-5-yl)-3,4-dihydro-1H-2,6-naphthyridine

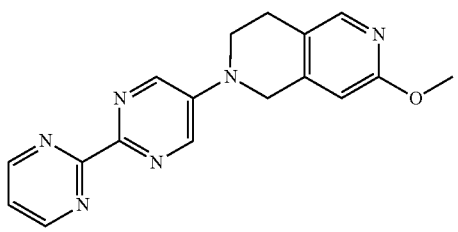 [SMILES: COc1cc2c(cn1)CCN(c1cnc(-c3ncccn3)nc1)C2]

To a mixture of 7-methoxy-1,2,3,4-tetrahydro-2,6-naphthyridine (50 mg, 0.30 mmol) in 1,4-dioxane (1 mL) was added 5-bromo-2-pyrimidin-2-yl-pyrimidine (108.28 mg, 0.460 mmol, the product of step 3 in Example 1), cesium carbonate (397 mg, 1.22 mmol, 4 eq) and Brettphos Pd G3 (15 mg, CAS registry number: 1470372-59-8). The resulting mixture was stirred at 120° C. for 12 hrs, then diluted with DCM (10 mL) and filtered. The filtrate was concentrated in vacuo and the residue purified by prep-HPLC to give 7-methoxy-2-(2-pyrimidin-2-ylpyrimidin-5-yl)-3,4-dihydro-1H-2,6-naphthyridine (8 mg) as a yellow solid. 1H NMR (400 MHz, Methanol-$d_4$) δ ppm: 8.92 (d, 2H), 8.68 (s, 2H), 8.04 (s, 1H), 7.52 (t, 1H), 6.74 (s, 1H), 4.63 (s, 2H), 3.83 (s, 3H), 3.75 (t, 2H), 2.91 (t, 2H). MS obsd. (ESI$^+$) [(M+H)$^+$]: 321.

Example 14

7-Methoxy-2-(2-pyrimidin-2-ylpyrimidin-5-yl)-3,4-dihydro-1H-isoquinoline

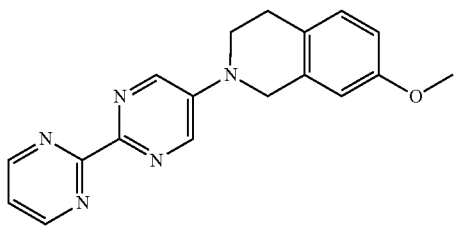 [SMILES: COc1ccc2c(c1)CN(c1cnc(-c3ncccn3)nc1)CC2]

To a mixture of 7-methoxy-1,2,3,4-tetrahydroisoquinoline (200 mg, 1.23 mmol), 5-bromo-2-pyrimidin-2-yl-pyrimidine (232 mg, 980 μmol, the product of step 3 in Example 1) and Cs$_2$CO$_3$ (2 g, 6.13 mmol) in dioxane (15 mL) was added Brettphos PD G3 (222 mg, 245 μmol, CAS registry number: 1470372-59-8). The resulting mixture was heated at 120° C. with stirring for 48 hrs under N$_2$. The mixture was filtered and the filtration was concentrated in vacuo. The residue was purified by Prep-HPLC to give 7-methoxy-2-(2-pyrimidin-2-ylpyrimidin-5-yl)-3,4-dihydro-1H-isoquinoline as a yellow solid (84 mg) as light yellow solid. 1H NMR (400 MHz, Methanol-$d_4$) δ ppm: 8.77-8.92 (m, 2H), 8.52 (s, 2H), 7.34-7.47 (m, 1H), 6.96-7.06 (m, 1H), 6.64-6.77 (m, 2H), 4.45-4.54 (m, 2H), 3.69 (s, 3H), 3.59-3.66 (m, 2H), 2.80-2.89 (m, 2H). MS obsd. (ESI$^+$) [(M+H)$^+$]: 320

Example 15

7-Cyclopropyl-2-(2-pyrimidin-2-ylpyrimidin-5-yl)-3,4-dihydro-1H-isoquinoline

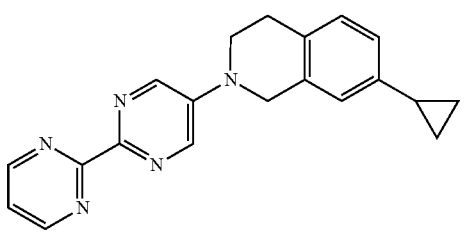 [SMILES: c1cnc(-c2ncc(N3CCc4ccc(C5CC5)cc4C3)cn2)nc1]

Step 1: Preparation of tert-butyl 7-bromo-3,4-dihydro-1H-isoquinoline-2-carboxylate

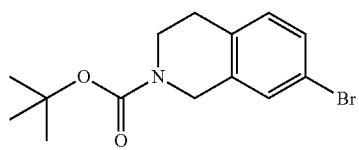 [SMILES: CC(C)(C)OC(=O)N1CCc2ccc(Br)cc2C1]

A mixture of 7-bromo-1,2,3,4-tetrahydroisoquinoline (1.5 g, 7.07 mmol), Boc$_2$O (3.09 g, 14.1 mmol) and DIPEA (914 mg, 1.24 mL, 7.07 mmol) in THF (30 mL) was stirred at rt. 3 hrs. The resulting mixture was concentrated in vacuo and the residue was purified by column (eluting with PE/EA=5/1, v:v) to give tert-butyl 7-bromo-3,4-dihydro-1H-isoquinoline-2-carboxylate (2.2 g) as light yellow oil.

Step 2: Preparation of tert-butyl 7-cyclopropyl-3,4-dihydro-1H-isoquinoline-2-carboxylate

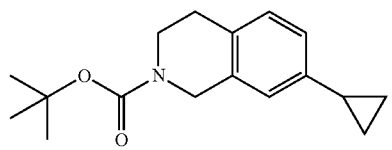 [SMILES: CC(C)(C)OC(=O)N1CCc2ccc(C3CC3)cc2C1]

A mixture of tert-butyl 7-bromo-3,4-dihydro-1H-isoquinoline-2-carboxylate (600 mg, 1.92 mmol), cyclopropylboronic acid (660 mg, 7.69 mmol), K$_3$PO$_4$ (1.63 g, 7.69 mmol), tricyclohexylphosphine (108 mg, 384 μmol) and Pd(OAc)$_2$ (43.1 mg, 192 μmol) in toluene (20 mL) was heated at 110° C. with stirring under N$_2$ overnight. The resulting mixture was concentrated in vacuo and the residue was purified by column (eluting with DCM:MeOH=40:1, v:v) to give tert-butyl 7-cyclopropyl-3,4-dihydro-1H-isoquinoline-2-carboxylate (400 mg) as colorless oil.

Step 3: Preparation of 7-cyclopropyl-1,2,3,4-tetrahydroisoquinoline hydrochloride

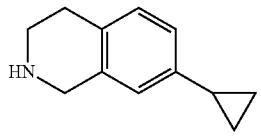

To a solution of tert-butyl 7-cyclopropyl-3,4-dihydro-1H-isoquinoline-2-carboxylate (400 mg, 1.46 mmol) in MeOH (20 mL) was added a solution HCl (0.5 mL, 1.0 M) in EA. The resulting mixture was stirred at rt for 3 hrs and then concentrated in vacuo to give crude 7-cyclopropyl-1,2,3,4-tetrahydroisoquinoline hydrochloride (260 mg) as white solid which was used in the next step directly without any further purification.

Step 4: Preparation of 7-cyclopropyl-2-(2-pyrimidin-2-ylpyrimidin-5-yl)-3,4-dihydro-1H-isoquinoline

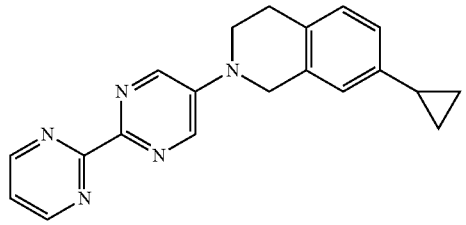 [SMILES: c1cnc(-c2ncc(N3CCc4ccc(C5CC5)cc4C3)cn2)nc1]

To a mixture of 7-cyclopropyl-1,2,3,4-tetrahydroisoquinoline (250 mg, 1.44 mmol), 5-bromo-2-pyrimidin-2-yl-pyrimidine (274 mg, 1.15 mmol, the product of step 3 in Example 1) and $Cs_2CO_3$ (2.35 g, 7.21 mmol) in dioxane (15 mL) was added Brettphos PD G3 (262 mg, 289 μmol, CAS registry number: 1470372-59-8). The resulting mixture was heated at 120° C. with stirring for 48 hrs. After being cooled to rt, the resulting mixture was filtered and the filtrate was concentrated in vacuo. The residue was purified by prep-HPLC to give 7-cyclopropyl-2-(2-pyrimidin-2-ylpyrimidin-5-yl)-3,4-dihydro-1H-isoquinoline (103 mg) as light yellow solid. $^1$H NMR (400 MHz, $CDCl_3$) δ ppm: 0.65-0.76 (m, 2H), 0.94-1.07 (m, 2H), 1.92 (s, 1H), 3.05 (s, 2H), 3.78 (t, 2H), 4.63 (s, 2H), 6.99 (s, 2H), 7.11-7.18 (m, 1H), 7.48-7.59 (m, 1H), 8.63-8.86 (m, 2H), 8.94-9.18 (m, 2H). MS obsd. (ESI$^+$) [(M+H)$^+$]: 330.

Example 16

N,N-Dimethyl-2-(2-pyrimidin-2-ylpyrimidin-5-yl)-3,4-dihydro-1H-isoquinolin-7-amine

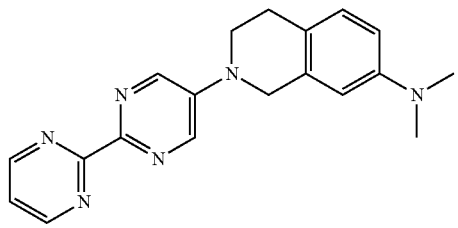 [SMILES: CN(C)c1ccc2c(c1)CN(c1cnc(-c3ncccn3)nc1)CC2]

Step 1: Preparation of tert-butyl 7-(dimethylamino)-3,4-dihydro-1H-isoquinoline-2-carboxylate

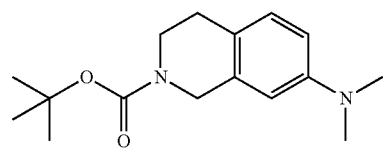 [SMILES: CN(C)c1ccc2c(c1)CN(C(=O)OC(C)(C)C)CC2]

A mixture of tert-butyl 7-bromo-3,4-dihydro-1H-isoquinoline-2-carboxylate (300 mg, 961 μmol), dimethylamine hydrochloride (235 mg, 2.88 mmol), sodium tert-butoxide (462 mg, 4.8 mmol), Ruphos (44.8 mg, 96.1 μmol) and $Pd_2(dba)_3$ (44 mg, 48 μmol) in dioxane (10 mL) was heated at 110° C. with stirring overnight. The resulting mixture was concentrated in vacuo and the residue was purified by column (eluting with DCM:MeOH=40:1, v:v) to give tert-butyl 7-(dimethylamino)-3,4-dihydro-1H-isoquinoline-2-carboxylate (220 mg) as yellow oil.

Step 2: Preparation of N,N-dimethyl-1,2,3,4-tetrahydroisoquinolin-7-amine

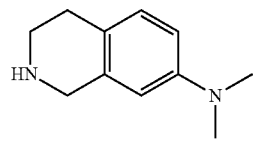

To a solution of tert-butyl 7-(dimethylamino)-3,4-dihydro-1H-isoquinoline-2-carboxylate (220 mg, 796 μmol) in MeOH (10 mL) was added a solution of HCl (0.5 mL, 1.0 M) in EA. The resulting mixture was stirred at rt for 3 hrs and then concentrated in vacuo to give crude N,N-dimethyl-1,2,3,4-tetrahydroisoquinolin-7-amine hydrochloride (150 mg) as light yellow solid which was used in the next step directly without any further purification.

Step 3: Preparation of N,N-dimethyl-2-(2-pyrimidin-2-ylpyrimidin-5-yl)-3,4-dihydro-1H-isoquinolin-7-amine

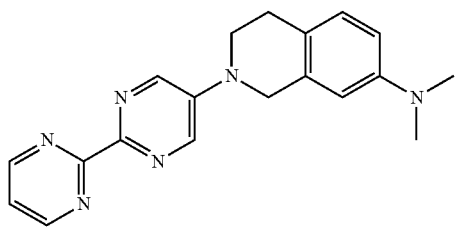 [SMILES: CN(C)c1ccc2c(c1)CN(c1cnc(-c3ncccn3)nc1)CC2]

To a mixture of 5-bromo-2-pyrimidin-2-yl-pyrimidine (161 mg, 681 μmol, the product of step 3 in Example 1), N,N-dimethyl-1,2,3,4-tetrahydroisoquinolin-7-amine (150 mg, 851 μmol) and $Cs_2CO_3$ (1.39 g, 4.26 mmol) in dioxane (5 mL) was added Brettphos PD G3 (38.6 mg, 42.6 μmol, CAS registry number: 1470372-59-8). The resulting mixture was heated at 110° C. with stirring overnight and then filtered. The filtrate was concentrated in vacuo. The residue was purified by prep-HPLC to give N,N-dimethyl-2-(2-pyrimidin-2-ylpyrimidin-5-yl)-3,4-dihydro-1H-isoquinolin-7-amine (90 mg) as light yellow solid. $^1$H NMR (400 MHz, DMSO-$d_6$) δ ppm: 2.87 (s, 8H), 3.66-3.74 (m, 2H), 4.52-4.60 (m, 2H), 6.65 (br s, 2H), 7.03 (d, 1H), 7.51 (s, 1H), 8.65 (s, 2H), 8.87-8.97 (m, 2H). MS obsd. (ESI$^+$) [(M+H)$^+$]: 333.

Example 17

7-Methyl-2-(2-pyrimidin-2-ylpyrimidin-5-yl)-3,4-dihydro-1H-isoquinoline

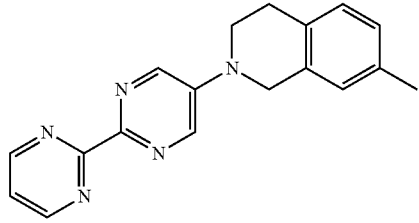 [SMILES: Cc1ccc2c(c1)CN(c1cnc(-c3ncccn3)nc1)CC2]

Step 1: Preparation of tert-butyl 7-methyl-3,4-dihydro-1H-isoquinoline-2-carboxylate

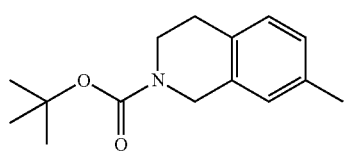 [SMILES: Cc1ccc2c(c1)CN(C(=O)OC(C)(C)C)CC2]

A mixture of tert-butyl 7-bromo-3,4-dihydro-1H-isoquinoline-2-carboxylate (300 mg, 961 μmol), 2,4,6-trimethyl-1,3,5,2,4,6-trioxatriborinane (603 mg, 4.8 mmol), $Pd_2(dba)_3$ (44 mg, 48 μmol), $PdCl_2(dppf)$ (42.2 mg, 96.1 μmol) and potassium carbonate (266 mg, 1.92 mmol) in dioxane (10 mL) and water (1 mL) was heated at 110° C. with stirring overnight. The resulting mixture was diluted with $H_2O$ (20 mL) and extracted with DCM (30 mL) for three times. The combined DCM layer was dried over anhydrous $Na_2SO_4$ and concentrated in vacuo. The residue was purified by column (eluting with PE/EA=5/1, v:v) to give tert-butyl 7-methyl-3,4-dihydro-1H-isoquinoline-2-carboxylate (200 mg) as yellow oil.

Step 2: Preparation of 7-methyl-1,2,3,4-tetrahydroisoquinoline

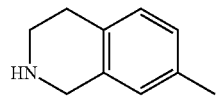

To a solution of tert-butyl 7-methyl-3,4-dihydro-1H-isoquinoline-2-carboxylate (200 mg, 809 μmol) in MeOH (10 mL) was added a solution of HCl (0.5 mL, 1.0 M) in EA. The resulting mixture was stirred at rt overnight and then concentrated in vacuo to give crude 7-methyl-1,2,3,4-tetrahydroisoquinoline hydrochloride (120 mg) as light yellow solid which was used in the next step directly without any further purification.

Step 3: Preparation of 7-methyl-2-(2-pyrimidin-2-ylpyrimidin-5-yl)-3,4-dihydro-1H-isoquinoline

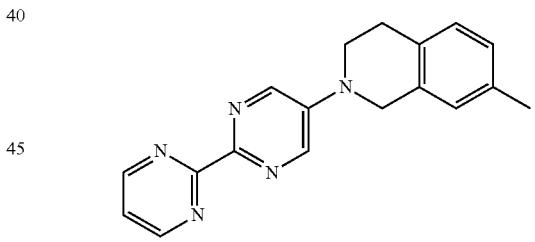

To a mixture of 5-bromo-2-pyrimidin-2-yl-pyrimidine (155 mg, 652 μmol, the product of step 3 in Example 1), 7-methyl-1,2,3,4-tetrahydroisoquinoline (120 mg, 815 μmol) and $Cs_2CO_3$ (1.33 g, 4.08 mmol) in dioxane (5 mL) was added Brettphos PD G3 (36.9 mg, 40.8 μmol, CAS registry number: 1470372-59-8). The resulting mixture was heated at 110° C. with stirring overnight and then filtered. The filtrate was purified by prep-HPLC to give 7-methyl-2-(2-pyrimidin-2-ylpyrimidin-5-yl)-3,4-dihydro-1H-isoquinoline (40 mg) as light yellow solid. $^1$H NMR (400 MHz, CDCl$_3$) δ ppm: 2.37 (s, 3H), 3.04 (s, 2H), 3.74 (s, 2H), 4.58 (s, 2H), 7.09 (s, 3H), 7.32-7.40 (m, 1H), 8.53-8.73 (m, 2H), 8.88-9.15 (m, 2H). MS obsd. (ESI$^+$) [(M+H)$^+$]: 304.

Example 18

N-Methyl-2-(2-pyrimidin-2-ylpyrimidin-5-yl)-3,4-dihydro-1H-isoquinolin-7-amine

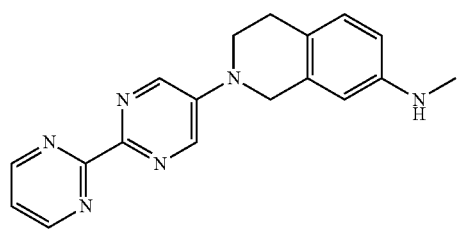

Step 1: Preparation of tert-butyl 7-(methylamino)-3,4-dihydro-1H-isoquinoline-2-carboxylate

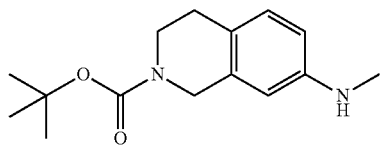 [SMILES: CNc1ccc2c(c1)CN(C(=O)OC(C)(C)C)CC2]

A mixture of tert-butyl 7-bromo-3,4-dihydro-1H-isoquinoline-2-carboxylate (600 mg, 1.92 mmol), copper (I) iodide (36.6 mg, 192 µmol) and an aqueous solution of methanamine (10 mL) was heated at 100° C. under N$_2$ with stirring overnight. The resulting mixture was extracted with EA (30 mL) for three times. The combined EA layer was dried over anhydrous Na$_2$SO$_4$ and concentrated in vacuo. The residue was purified by column (eluting with PE/EA=1/1, v:v) to give tert-butyl 7-(methylamino)-3,4-dihydro-1H-isoquinoline-2-carboxylate (159 mg) as yellow solid.

Step 2: Preparation of N-methyl-1,2,3,4-tetrahydroisoquinolin-7-amine

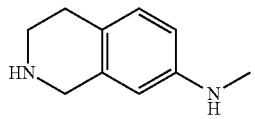

To a solution of tert-butyl 7-(methylamino)-3,4-dihydro-1H-isoquinoline-2-carboxylate (90 mg, 343 µmol) in MeOH (10 mL) was added a solution of HCl (0.5 mL, 1.0 M). The resulting mixture was stirred at rt overnight and then concentrated in vacuo to give crude N-methyl-1,2,3,4-tetrahydroisoquinolin-7-amine (60 mg) as white solid which was used in the next step directly without any further purification.

Step 3: Preparation of N-methyl-2-(2-pyrimidin-2-ylpyrimidin-5-yl)-3,4-dihydro-1H-isoquinolin-7-amine

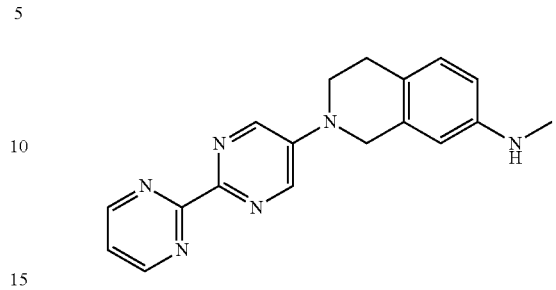

To a mixture of 5-bromo-2-pyrimidin-2-yl-pyrimidine (70.1 mg, 296 µmol, the product of step 3 in Example 1), N-methyl-1,2,3,4-tetrahydroisoquinolin-7-amine (60 mg, 370 µmol) and Cs$_2$CO$_3$ (603 mg, 1.85 mmol) in dioxane (5 mL) was added BRETTPHOS Pd G3 (16.8 mg, 18.5 µmol). The resulting mixture was heated at 110° C. with stirring overnight and then filtered. The filtrated was purified by prep-HPLC to give N-methyl-2-(2-pyrimidin-2-ylpyrimidin-5-yl)-3,4-dihydro-1H-isoquinolin-7-amine (20 mg) as light yellow solid. $^1$H NMR (400 MHz, CDCl$_3$) δ ppm: 2.89 (s, 3H), 2.93-3.01 (m, 2H), 3.66-3.76 (m, 2H), 4.53 (s, 2H), 6.54-6.69 (m, 2H), 7.06 (d, 1H), 7.30-7.35 (m, 1H), 8.59 (s, 2H), 8.95 (d, 2H). MS obsd. (ESI$^+$) [(M+H)$^+$]: 319.

Example 19

7-(2,2-Difluoroethoxy)-5-fluoro-2-(2-pyrimidin-2-ylpyrimidin-5-yl)-3,4-dihydro-1H-isoquinoline

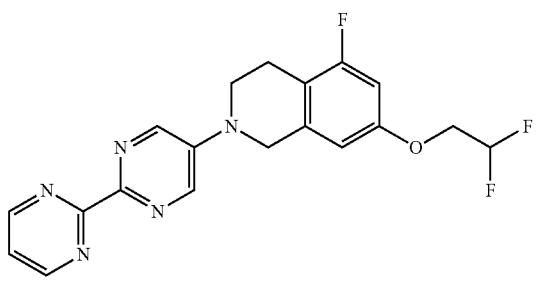 [SMILES: Fc1cc(OCC(F)F)cc2c1CCN(c1cnc(-c3ncccn3)nc1)C2]

Step 1: Preparation of 5-fluoro-2-(2-pyrimidin-2-ylpyrimidin-5-yl)-3,4-dihydro-1H-isoquinolin-7-ol

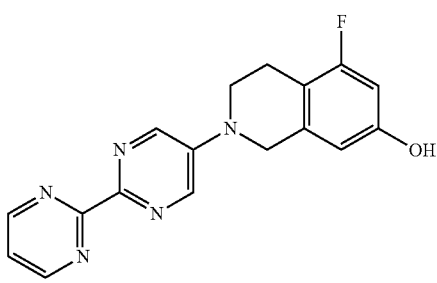 [SMILES: Oc1cc(F)c2c(c1)CN(c1cnc(-c3ncccn3)nc1)CC2]

To a solution of 5-fluoro-7-methoxy-2-(2-pyrimidin-2-ylpyrimidin-5-yl)-3,4-dihydro-1H-isoquinoline (800 mg, 2.37 mmol, Example 5) in DCM (15 mL), which was cooled at −10° C., was added boron tribromide (1.78 g, 7.11 mmol) slowly and the reaction mixture was stirred at 0° C. for 2 hrs. The reaction was quenched with MeOH (5 mL). The resulting mixture was neutralized with basic resin and filtered. The filtrate was concentrated in vacuo to afford 5-fluoro-2-(2-pyrimidin-2-ylpyrimidin-5-yl)-3,4-dihydro-1H-isoquinolin-7-ol (720 mg) as a yellow solid, which was used in the next step directly without any further purification.

Step 2: Preparation of 7-(2,2-difluoroethoxy)-5-fluoro-2-(2-pyrimidin-2-ylpyrimidin-5-yl)-3,4-dihydro-1H-isoquinoline

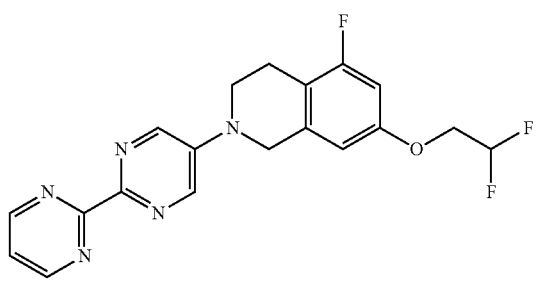 [SMILES: Fc1cc(OCC(F)F)cc2c1CCN(c1cnc(-c3ncccn3)nc1)C2]

A mixture of 5-fluoro-2-(2-pyrimidin-2-ylpyrimidin-5-yl)-3,4-dihydro-1H-isoquinolin-7-ol (100 mg, 0.31 mmol), 2-bromo-1,1-difluoroethane (54 mg, 0.37 mmol) and potassium carbonate (64 mg, 0.46 mmol) in DMF (2 mL) was stirred at 70° C. for 16 hrs. The resulting reaction mixture was cooled and filtered. The filtrate was purified by prep-HPLC to afford 7-(2,2-difluoroethoxy)-5-fluoro-2-(2-pyrimidin-2-ylpyrimidin-5-yl)-3,4-dihydro-1H-isoquinoline (56 mg) as a white solid. $^1$H NMR (400 MHz, Methanol-d$_4$) δ ppm: 8.95 (d, 2H), 8.68 (s, 2H), 7.52 (t, 1H), 6.79 (s, 1H), 6.69 (dd, 1H), 6.02-6.34 (m, 1H), 4.65 (s, 2H), 4.24 (td, 2H), 3.81 (t, 2H), 2.94 (t, 2H). MS obsd. (ESI$^+$) [(M+H)$^+$]: 370.

Example 20

2-(2-Pyrimidin-2-ylpyrimidin-5-yl)-3,4-dihydro-1H-isoquinoline-7-carbonitrile

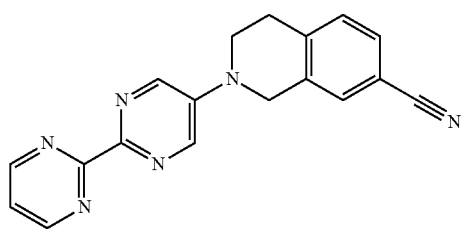 [SMILES: N#Cc1ccc2c(c1)CN(c1cnc(-c3ncccn3)nc1)CC2]

Step 1: Preparation of tert-butyl 7-cyano-3,4-dihydro-1H-isoquinoline-2-carboxylate

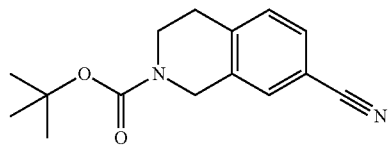 [SMILES: CC(C)(C)OC(=O)N1CCc2ccc(C#N)cc2C1]

A mixture of tert-butyl 7-bromo-3,4-dihydro-1H-isoquinoline-2-carboxylate (600 mg, 1.92 mmol), Zinc cyanide (1.13 g, 9.61 mmol) and Pd(PPh$_3$)$_4$ (220 mg, 0.19 mmol) in DMF (10 mL) was heated at 110° C. with stirring overnight. The resulting mixture was filtered and the filtrate was concentrated in vacuo. The residue was purified by column (eluting with PE/EA=1/1, v:v) to give tert-butyl 7-cyano-3,4-dihydro-1H-isoquinoline-2-carboxylate (129 mg) as white solid.

Step 2: Preparation of 1,2,3,4-tetrahydroisoquinoline-7-carbonitrile

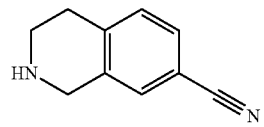 [SMILES: N#Cc1ccc2c(c1)CNCC2]

To a solution of tert-butyl 7-cyano-3,4-dihydro-1H-isoquinoline-2-carboxylate (129 mg, 499 μmol) in MeOH (10 mL) was added a solution of HCl (0.5 mL, 1.0 M) in EA. The resulting mixture was stirred at rt overnight and then concentrated in vacuo to give crude 1,2,3,4-tetrahydroisoquinoline-7-carbonitrile (80 mg) as white solid which was used in the next step directly without any further purification.

Step 3: Preparation of 2-(2-pyrimidin-2-ylpyrimidin-5-yl)-3,4-dihydro-1H-isoquinoline-7-carbonitrile

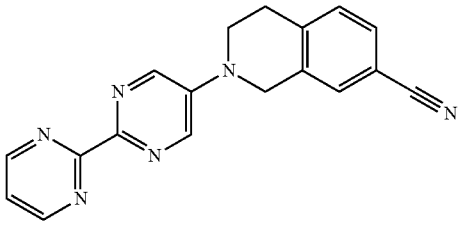

To a mixture of 5-bromo-2-pyrimidin-2-yl-pyrimidine (95.9 mg, 405 μmol, the product of step 3 in Example 1), 1,2,3,4-tetrahydroisoquinoline-7-carbonitrile (80 mg, 506 μmol) and Cs$_2$CO$_3$ (824 mg, 2.53 mmol) in dioxane (5 mL) was added Brettphos PD G3 (16.8 mg, 18.5 μmol, CAS registry number: 1470372-59-8). The resulting mixture was heated at 110° C. with stirring overnight and filtered. The filtrate was purified by prep-HPLC to give 2-(2-pyrimidin-2-ylpyrimidin-5-yl)-3,4-dihydro-1H-isoquinoline-7-carbonitrile (28 mg) as light yellow solid. $^1$H NMR (400 MHz, CDCl$_3$) δ ppm: 3.13-3.21 (m, 2H), 3.77-3.86 (m, 2H), 4.68 (s, 2H), 7.38 (d, 1H), 7.42-7.51 (m, 1H), 7.54-7.64 (m, 2H), 8.73 (br s, 2H), 9.07 (br s, 2H). MS obsd. (ESI$^+$) [(M+H)$^+$]: 315.

Example 21

7-(Cyclopropylmethoxy)-5-fluoro-2-(2-pyrimidin-2-ylpyrimidin-5-yl)-3,4-dihydro-1H-isoquinoline

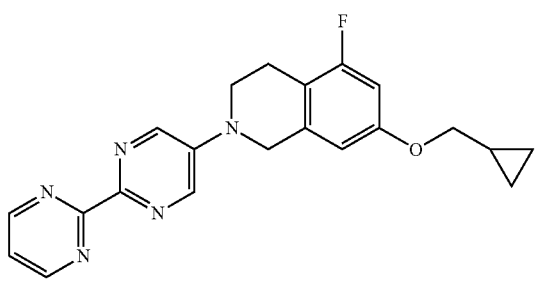 [SMILES: Fc1cc(OCC2CC2)cc2c1CCN(c1cnc(-c3ncccn3)nc1)C2]

A mixture of 5-fluoro-2-(2-pyrimidin-2-ylpyrimidin-5-yl)-3,4-dihydro-1H-isoquinolin-7-ol (100 mg, 0.31 mmol, the product of step 1 in Example 19), (bromomethyl) cyclopropane (50 mg, 0.37 mmol) and potassium carbonate (64 mg, 0.46 mmol) in DMF (2 mL) was stirred at 70° C. for 16 hrs. The reaction mixture was cooled to rt and filtered. The filtrate was purified by prep-HPLC to afford 7-(cyclopropylmethoxy)-5-fluoro-2-(2-pyrimidin-2-ylpyrimidin-5-yl)-3,4-dihydro-1H-isoquinoline (20.1 mg) as a white solid. $^1$H NMR (400 MHz, Methanol-d$_4$) δ ppm: 8.94 (d, 2H), 8.66 (s, 2H), 7.52 (t, 1H), 6.70 (s, 1H), 6.58 (dd, 1H), 4.62 (s, 2H), 3.76-3.85 (m, 4H), 2.92 (t, 2H), 1.17-1.33 (m, 1H), 0.57-0.68 (m, 2H), 0.30-0.39 (m, 2H). MS obsd. (ESI$^+$) [(M+H)$^+$]: 378.

Example 22

7-Chloro-2-(2-pyrimidin-2-ylpyrimidin-5-yl)-3,4-dihydro-1H-isoquinoline

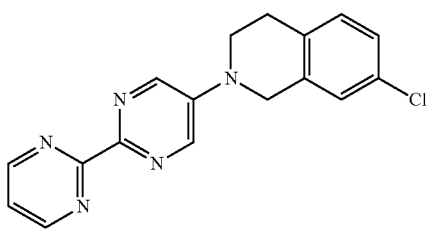 [SMILES: Clc1ccc2c(c1)CN(c1cnc(-c3ncccn3)nc1)CC2]

To a mixture of 7-chloro-1,2,3,4-tetrahydroisoquinoline (200 mg, 1.19 mmol), 5-bromo-2-pyrimidin-2-yl-pyrimidine (226 mg, 954 μmol, the product of step 3 in Example 1) and Cs$_2$CO$_3$ (1.94 g, 5.97 mmol) in dioxane (15 mL) was added Brettphos Pd G3 (216 mg, 239 μmol, CAS registry number: 1470372-59-8). The resulting mixture was heated at 120° C. with stirring for 48 hrs under N$_2$ and filtered. The filtrate was concentrated in vacuo. The residue was purified by prep-HPLC to give 7-chloro-2-(2-pyrimidin-2-ylpyrimidin-5-yl)-3,4-dihydro-1H-isoquinoline (26 mg) as light yellow solid. $^1$H NMR (400 MHz, Methanol-d$_4$) δ ppm: 8.87-8.99 (m, 2H), 8.55-8.70 (m, 2H), 7.45-7.59 (m, 1H), 7.25-7.38 (m, 1H), 7.21 (s, 2H), 4.62 (s, 2H), 3.76 (t, 2H), 3.02 (s, 2H). MS obsd. (ESI$^+$) [(M+H)$^+$]: 324.

Example 23

N,N-Dimethyl-2-(2-pyrimidin-2-ylpyrimidin-5-yl)-3,4-dihydro-1H-isoquinolin-6-amine

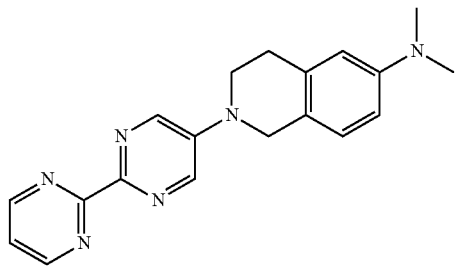 [SMILES: CN(C)c1ccc2c(c1)CCN(c1cnc(-c3ncccn3)nc1)C2]

Step 1: Preparation of tert-butyl 6-bromo-3,4-dihydro-1H-isoquinoline-2-carboxylate

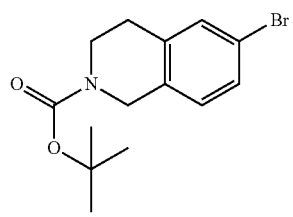 [SMILES: CC(C)(C)OC(=O)N1CCc2cc(Br)ccc2C1]

A mixture of 6-bromo-1,2,3,4-tetrahydroisoquinoline (2 g, 9.43 mmol), Boc$_2$O (2.26 g, 2.41 mL, 10.4 mmol) and Et$_3$N (1.91 g, 2.63 mL, 18.9 mmol) in THF (30 mL) was stirred at rt. For 3 hrs. The resulting mixture was diluted with aqueous Na$_2$CO$_3$ solution and extracted with EA (30 mL) twice. The combined organic layer was washed with brine, dried over aqueous Na$_2$SO$_4$, filtered, and concentrated in vacuo to afford tert-butyl 6-bromo-3,4-dihydro-1H-isoquinoline-2-carboxylate (2.9 g) as white solid which was directly used in the next step without any further purification.

Step 2: Preparation tert-butyl 6-(dimethylamino)-3,4-dihydro-1H-isoquinoline-2-carboxylate

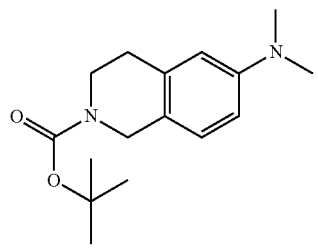 [SMILES: CN(C)c1ccc2c(c1)CCN(C(=O)OC(C)(C)C)C2]

A mixture of tert-butyl 6-bromo-3,4-dihydro-1H-isoquinoline-2-carboxylate (300 mg, 961 μmol), dimethylamine hydrochloride (235 mg, 2.88 mmol), sodium tert-butoxide (462 mg, 4.8 mmol), Ruphos (44.8 mg, 96.1 μmol) and pd₂(dba)₃ (44 mg, 48 μmol) in dioxane (10 mL) was heated at 110° C. overnight. Then the resulting mixture was concentrated in vacuo and the residue was purified by flash column (eluting with DCM:MeOH=40:1, v:v) to give tert-butyl 6-(dimethylamino)-3,4-dihydro-1H-isoquinoline-2-carboxylate as a yellow oil (240 mg).

Step 3: Preparation N,N-dimethyl-1,2,3,4-tetrahydroisoquinolin-6-amine hydrochloride

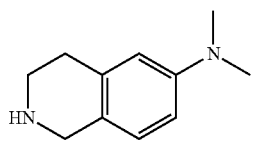

To a solution of tert-butyl 6-(dimethylamino)-3,4-dihydroisoquinoline-2(1H)-carboxylate (240 mg, 868 μmol) in MeOH (10 mL) was added HCl solution of methanol (10 mL). The resulting mixture was stirred at rt for 3 hrs and then concentrated in vacuo to give crude N,N-dimethyl-1,2,3,4-tetrahydroisoquinolin-6-amine hydrochloride (150 mg) which was used in the next step directly without any further purification.

Step 4: Preparation N,N-dimethyl-2-(2-pyrimidin-2-ylpyrimidin-5-yl)-3,4-dihydro-1H-isoquinolin-6-amine

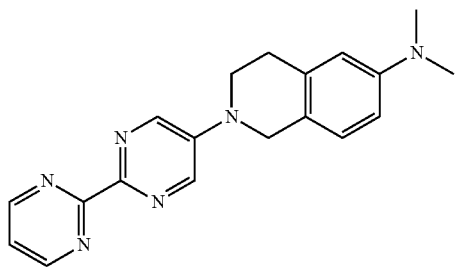 [SMILES: CN(C)c1ccc2c(c1)CCN(c1cnc(-c3ncccn3)nc1)C2]

To a mixture of N,N-dimethyl-1,2,3,4-tetrahydroisoquinolin-6-amine hydrochloride (150 mg, 851 μmol), 5-bromo-2-pyrimidin-2-yl-pyrimidine (161 mg, 681 μmol, the product of step 3 in Example 1) and Cs₂CO₃ (1.39 g, 4.26 mmol) in dioxane (15 mL) was added Brettphos Pd G3 (154 mg, 170 μmol, CAS registry number: 1470372-59-8). The resulting mixture was heated at 120° C. with stirring for 48 hrs under N₂. Then the mixture was filtered and the filtrate was concentrated in vacuo. The residue was purified by prep-HPLC to give N,N-dimethyl-2-(2-pyrimidin-2-ylpyrimidin-5-yl)-3,4-dihydro-1H-isoquinolin-6-amine as a yellow solid (120 mg) as light yellow solid. ¹H NMR (400 MHz, Methanol-d₄) δ ppm: 8.81 (d, 2H), 8.46 (s, 2H), 7.37 (t, 1H), 6.98 (d, 1H), 6.43-6.63 (m, 2H), 4.38 (s, 2H), 3.58 (t, 2H), 2.83-2.89 (m, 2H), 2.80 (s, 6H). MS obsd. (ESI⁺) [(M+H)⁺]: 333.

Example 24

6-Cyclopropyl-2-(2-pyrimidin-2-ylpyrimidin-5-yl)-3,4-dihydro-1H-isoquinoline

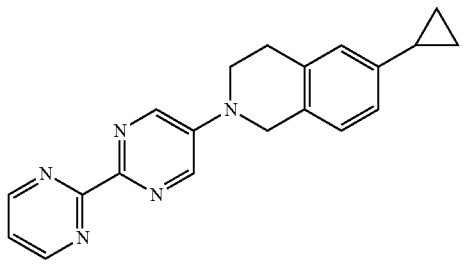 [SMILES: c1cnc(-c2ncc(N3CCc4cc(C5CC5)ccc4C3)cn2)nc1]

Step 1: Preparation of tert-butyl 6-cyclopropyl-3,4-dihydro-1H-isoquinoline-2-carboxylate

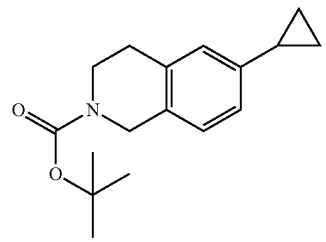 [SMILES: CC(C)(C)OC(=O)N1CCc2cc(C3CC3)ccc2C1]

A mixture of tert-butyl 6-bromo-3,4-dihydro-1H-isoquinoline-2-carboxylate (700 mg, 2.24 mmol), cyclopropylboronic acid (770 mg, 8.97 mmol), potassium phosphate tribasic (1.9 g, 8.97 mmol), tricyclohexylphosphine (126 mg, 448 μmol) and Pd(OAc)₂ (50.3 mg, 224 μmol) in toluene (20 mL) was heated at 110° C. with stirring overnight under N₂. The resulting mixture was concentrated in vacuo and the residue was purified by column (eluting with DCM:MeOH=40:1, v:v) to give tert-butyl 6-cyclopropyl-3,4-dihydro-1H-isoquinoline-2-carboxylate (400 mg) as a colorless oil.

Step 2: Preparation of 6-cyclopropyl-1,2,3,4-tetrahydroisoquinoline hydrochloride

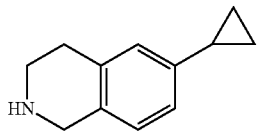 [SMILES: c1cc2c(cc1C1CC1)CCNC2]

To a solution of tert-butyl 6-cyclopropyl-3,4-dihydroisoquinoline-2(1H)-carboxylate (400 mg, 1.46 mmol) in MeOH (10 mL) was added HCl solution of methanol (10 mL). The resulting mixture was stirred at rt for 3 hrs and then concentrated in vacuo to give crude 6-cyclopropyl-1,2,3,4-tetrahydroisoquinoline hydrochloride (200 mg) which was used in the next step directly without any further purification.

Step 3: Preparation of 6-cyclopropyl-2-(2-pyrimidin-2-ylpyrimidin-5-yl)-3,4-dihydro-1H-isoquinoline

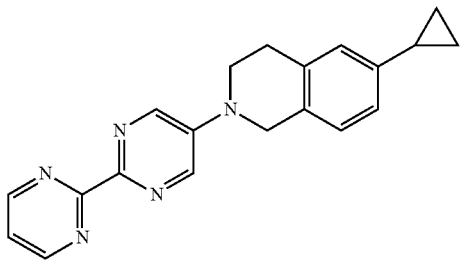 [SMILES: c1cnc(-c2ncc(N3CCc4cc(C5CC5)ccc4C3)cn2)nc1]

To a mixture of 6-cyclopropyl-1,2,3,4-tetrahydroisoquinoline hydrochloride (150 mg, 866 μmol), 5-bromo-2-pyrimidin-2-yl-pyrimidine (164 mg, 693 μmol, the product of step 3 in Example 1) and Cs$_2$CO$_3$ (1.41 g, 4.33 mmol) in dioxane (5 mL) was added Brettphos PD G3 (157 mg, 173 μmol, CAS registry number: 1470372-59-8). The resulting mixture was heated at 120° C. with stirring for 48 hrs under N$_2$ atmosphere and then filtered. The filtrate was concentrated in vacuo. The residue was purified by prep-HPLC to give 6-cyclopropyl-2-(2-pyrimidin-2-ylpyrimidin-5-yl)-3,4-dihydro-1H-isoquinoline yellow solid (29 mg) as light yellow solid. $^1$H NMR (400 MHz, Methanol-d$_4$) δ ppm: 8.82 (d, 2H), 8.50 (s, 2H), 7.34-7.45 (m, 1H), 7.00-7.13 (m, 1H), 6.77-6.91 (m, 2H), 4.39-4.53 (m, 2H), 3.54-3.72 (m, 2H), 2.82-2.96 (m, 2H), 1.70-1.88 (m, 1H), 0.77-0.92 (m, 2H), 0.48-0.67 (m, 2H). MS obsd. (ESI$^+$) [(M+H)$^+$]: 330.

Example 25

2-(2-Pyrimidin-2-ylpyrimidin-5-yl)-3,4-dihydro-1H-isoquinoline-5-carbonitrile

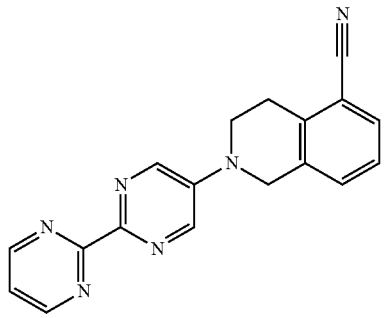 [SMILES: N#Cc1cccc2c1CCN(c1cnc(-c3ncccn3)nc1)C2]

Step 1: Preparation of 1,2,3,4-tetrahydroisoquinoline-5-carbonitrile

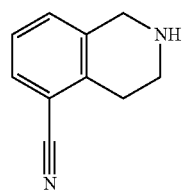 [SMILES: N#Cc1cccc2c1CCNC2]

To a solution of 5-bromo-1,2,3,4-tetrahydroisoquinoline (1.06 g, 10 mmol) in DMF (3 mL) was added zinc cyanide (875 mg, 7.5 mmol) and Pd(P(Ph$_3$)$_4$ (577 mg, 0.5 mmol). The resulting mixture was heated at 100° C. and stirred for 15 hrs under N$_2$, then poured into water (30 mL) and extracted with EA (50 mL) twice. The organic layers were combined and washed with water and brine, dried over anhydrous Na$_2$SO$_4$ and concentrated in vacuo. The residue was purified by column (eluting with DCM:MeOH=20:1, v:v) to give 1,2,3,4-tetrahydroisoquinoline-5-carbonitrile (400 mg) as a yellow solid.

Step 2: Preparation of 2-(2-pyrimidin-2-ylpyrimidin-5-yl)-3,4-dihydro-1H-isoquinoline-5-carbonitrile

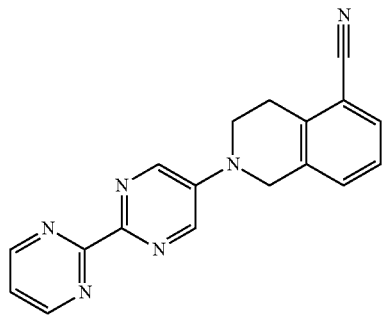 [SMILES: N#Cc1cccc2c1CCN(c1cnc(-c3ncccn3)nc1)C2]

To a solution of 5-bromo-2-pyrimidin-2-yl-pyrimidine (711 mg, 3 mmol, the product of step 3 in Example 1) and 1,2,3,4-tetrahydroisoquinoline-5-carbonitrile (395 mg, 2.5 mmol) in 1,4-dioxane (5 mL) was added BrettPhos Pd G3 (113 mg, 0.125 mmol, CAS registry number: 1470372-59-8) and cesium carbonate (1.63 g, 5 mmol). The resulting mixture was heated at 110° C. with stirring for 15 hrs under N$_2$, then poured into water (30 mL) and extracted with DCM (50 mL) twice. The organic layers were combined, then washed with water and brine, dried over anhydrous Na$_2$SO$_4$ and concentrated in vacuo. The residue was purified by prep-HPLC to provide 2-(2-pyrimidin-2-ylpyrimidin-5-yl)-3,4-dihydro-1H-isoquinoline-5-carbonitrile (6 mg) as an off-white powder. $^1$H NMR (400 MHz, CDCl$_3$) δ ppm: 8.99 (d, 2H), 8.67 (s, 2H), 7.62 (d, 1H), 7.51 (d, 1H), 7.35-7.42 (m, 2H), 4.63 (s, 2H), 3.83 (t, 2H), 3.30 (t, 2H). MS obsd. (ESI$^+$) [(M+H)$^+$]: 315.

Example 26

7-(3-Methoxyazetidin-1-yl)-2-(2-pyrimidin-2-ylpyrimidin-5-yl)-3,4-dihydro-1H-isoquinoline

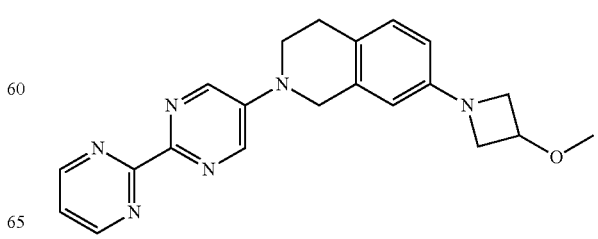

Step 1: Preparation of tert-butyl 7-(3-methoxyazetidin-1-yl)-3,4-dihydro-1H-isoquinoline-2-carboxylate

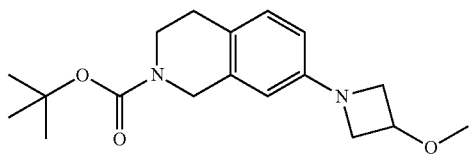 [SMILES: COC1CN(c2ccc3c(c2)CN(C(=O)OC(C)(C)C)CC3)C1]

A mixture of tert-butyl 7-bromo-3,4-dihydro-1H-isoquinoline-2-carboxylate (450 mg, 1.44 mmol), 3-methoxyazetidine hydrochloride (178 mg, 1.44 mmol), sodium tert-butoxide (693 mg, 7.21 mmol), Ruphos (67.3 mg, 144 μmol) and Pd$_2$(dba)$_3$ (66 mg, 72.1 μmol) in dioxane (10 mL) was heated at 110° C. with stirring overnight. The resulting mixture was concentrated in vacuo and the residue was purified by column (eluting with PE/EA=1/1, v:v) to give tert-butyl 7-(3-methoxyazetidin-1-yl)-3,4-dihydro-1H-isoquinoline-2-carboxylate (290 mg) as yellow oil.

Step 2: Preparation of 7-(3-methoxyazetidin-1-yl)-1,2,3,4-tetrahydroisoquinoline hydrochloride

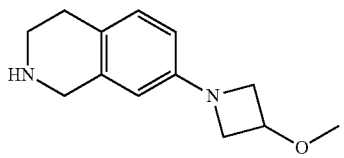 [SMILES: COC1CN(c2ccc3c(c2)CNCC3)C1]

To a solution of tert-butyl 7-(3-methoxyazetidin-1-yl)-3,4-dihydro-1H-isoquinoline-2-carboxylate (290 mg, 911 μmol) in dioxane (5 mL) was added hydrochloric acid (0.5 mL). The resulting mixture was stirred at rt for 3 hrs and then concentrated in vacuo to give crude 7-(3-methoxyazetidin-1-yl)-1,2,3,4-tetrahydroisoquinoline hydrochloride, which was used in the next step directly without any further purification.

Step 3: Preparation of 7-(3-methoxyazetidin-1-yl)-2-(2-pyrimidin-2-ylpyrimidin-5-yl)-3,4-dihydro-1H-isoquinoline

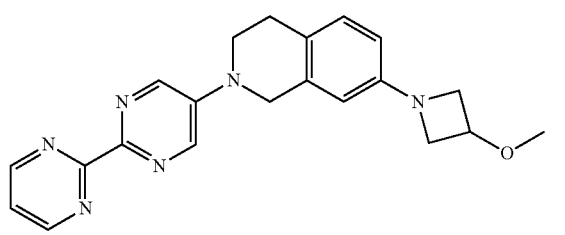 [SMILES: COC1CN(c2ccc3c(c2)CN(c2cnc(-c4ncccn4)nc2)CC3)C1]

A mixture of 5-bromo-2-pyrimidin-2-yl-pyrimidine (218 mg, 920 μmol, the product of step 3 in Example 1), 7-(3-methoxycyclobutyl)-1,2,3,4-tetrahydroisoquinoline (200 mg, 920 μmol), Brettphos PD G3 (41.7 mg, 46 μmol, CAS registry number: 1470372-59-8) and Cs$_2$CO$_3$ (1.5 g, 4.6 mmol) in dioxane (5 mL) was heated at 110° C. with stirring overnight. The resulting mixture was filtered and the filtrate was purified by prep-HPLC to give 7-(3-methoxyazetidin-1-yl)-2-(2-pyrimidin-2-ylpyrimidin-5-yl)-3,4-dihydro-1H-isoquinoline (30 mg) as yellow solid. $^1$H NMR (400 MHz, CDCl$_3$) δ ppm: 2.92 (s, 2H), 3.21-3.31 (m, 1H), 3.41-3.44 (m, 1H), 3.47 (s, 3H), 3.58-3.72 (m, 5H), 4.49 (s, 2H), 6.49-6.60 (m, 2H), 7.01 (d, 1H), 7.33 (s, 1H), 8.57 (s, 2H), 8.94 (br d, 2H). MS obsd. (ESI$^+$) [(M+H)$^+$]: 375.

Example 27

5-Fluoro-2-(2-pyrimidin-2-ylpyrimidin-5-yl)-3,4-dihydro-1H-isoquinoline

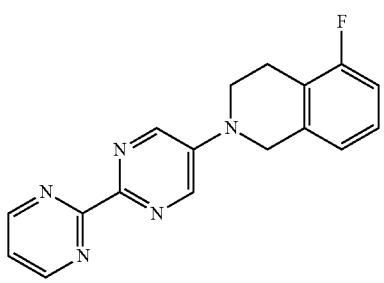 [SMILES: Fc1cccc2c1CCN(c1cnc(-c3ncccn3)nc1)C2]

Step 1: Preparation of 1-bromo-3-fluoro-2-[(E)-2-nitrovinyl]benzene

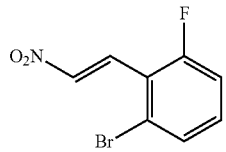 [SMILES: O=[N+]([O-])/C=C/c1c(F)cccc1Br]

A mixture of 2-bromo-6-fluorobenzaldehyde (15.0 g, 73.9 mmol) and NH$_4$Ac (14.24 g, 184.7 mmol) in AcOH (300 mL) was stirred at 120° C. for 4 hrs. The resulting mixture was diluted with water (1.2 L) and filtered. The filter cake was dried in vacuo to give 1-bromo-3-fluoro-2-[(E)-2-nitrovinyl]benzene (15 g) as yellow solid.

Step 2: Preparation of 1-bromo-3-fluoro-2-(2-nitroethyl)benzene

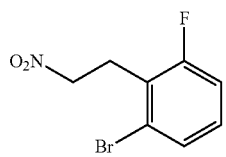 [SMILES: O=[N+]([O-])CCc1c(F)cccc1Br]

To a solution of 1-bromo-3-fluoro-2-[(E)-2-nitrovinyl]benzene (15.0 g, 57.7 mmol) in EtOH (300 mL) was added NaBH$_4$ (8.73 g, 230.7 mmol) in portions at 0° C. The resulting mixture was then warmed to rt and stirred for 3 hrs. The reaction was quenched with aqueous NH$_4$Cl (100 mL) and the resulting mixture was extracted with EA (200 mL) for three times. The combined organic phase was washed with brine (200 mL) and dried over Na$_2$SO$_4$ and filtered.

The filtrate was concentrated in vacuo. The residue was purified by flash column (eluting with PE/EA=20/1, v:v) to give 1-bromo-3-fluoro-2-(2-nitroethyl)benzene (10 g) as light-yellow oil.

Step 3: Preparation of 2-(2-bromo-6-fluoro-phenyl)ethanamine

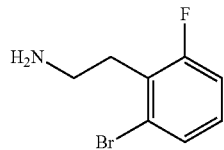 [SMILES: NCCc1c(F)cccc1Br]

To a solution of 1-bromo-3-fluoro-2-(2-nitroethyl)benzene (8.33 g, 33.6 mmol) in EtOH (50 mL) and water (50 mL) was added NH$_4$Cl (8.98 g, 167.9 mmol) and iron powder (9.38 g, 167.91 mmol). The resulting mixture was then heated at 80° C. with stirring for 1 hr and filtered. The filtrate was concentrated in vacuo. The residue was purified by column (eluting with DCM/MeOH=10/1, v:v) to give 2-(2-bromo-6-fluoro-phenyl)ethanamine (7 g) as a red solid.

Step 4: Preparation of 5-fluoro-3,4-dihydro-2H-isoquinolin-1-one

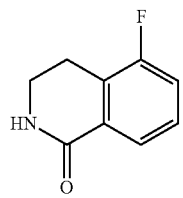 [SMILES: O=C1NCCc2c(F)cccc21]

To a solution of 2-(2-bromo-6-fluoro-phenyl)ethanamine (3.0 g, 13.8 mmol) in toluene (30 mL) was added butyldi-1-adamantylphosphine (1.97 g, 5.5 mmol), Na$_2$CO$_3$ (4.7 g, 41.3 mmol) and Pd$_2$(dba)$_3$ (2.52 g, 2.75 mmol). The resulting mixture was heated to 80° C. and stirred for 24 hrs under 2280 mmHg of CO. The reaction mixture was diluted with DCM (100 mL) and then washed with water (30 mL) and brine (30 mL), dried over anhydrous Na$_2$SO$_4$ and concentrated in vacuo. The residue was purified by column (eluting with DCM/MeOH=10/1, v:v) to give black oil, which was further purified by prep-HPLC to give 5-fluoro-3,4-dihydro-2H-isoquinolin-1-one (150 mg) as a white solid.

Step 5: Preparation of 5-fluoro-1,2,3,4-tetrahydroisoquinoline

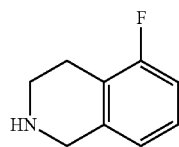

A solution of 5-fluoro-3,4-dihydro-2H-isoquinolin-1-one (150 mg, 0.91 mmol) in THF (1 mL) was added dropwise to a solution of LiAlH$_4$ (138 mg, 3.63 mmol) in THF (2 mL) at 0° C. The resulting mixture was stirred at 25° C. for 5 hrs. The reaction mixture was quenched with H$_2$O (0.14 mL) and 15% NaOH (0.14 mL) successively and the resulting mixture was filtered. The filtrate was concentrated in vacuo to afford 5-fluoro-1,2,3,4-tetrahydroisoquinoline (130 mg, crude) as a colorless oil which was used in the next step directly without any further purification.

Step 6: Preparation of tert-butyl 5-fluoro-3,4-dihydro-1H-isoquinoline-2-carboxylate

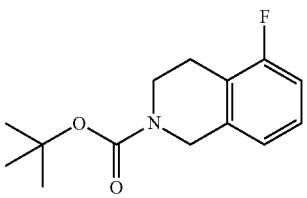 [SMILES: CC(C)(C)OC(=O)N1CCc2c(F)cccc2C1]

To a solution of 5-fluoro-1,2,3,4-tetrahydroisoquinoline (130 mg, 0.86 mmol) in DCM (2 mL) was added Boc$_2$O (282 mg, 1.29 mmol) and DIPEA (261 mg, 2.58 mmol). After being stirred at rt for 12 hrs and diluted with DCM (80 mL), the resulting mixture was washed with water (30 mL) and brine (30 mL), dried over anhydrous Na$_2$SO$_4$ and concentrated in vacuo. The residue was purified by column (eluting with PE/EA=30/1, v:v) to give tert-butyl 5-fluoro-3,4-dihydro-1H-isoquinoline-2-carboxylate (200 mg) as a yellow oil.

Step 7: Preparation of 5-fluoro-1,2,3,4-tetrahydroisoquinoline hydrochloride

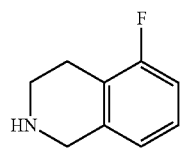

A mixture of tert-butyl 5-fluoro-3,4-dihydro-1H-isoquinoline-2-carboxylate (200 mg, 0.8 mmol) in a solution of HCl in MeOH (3 mL, 4.0 M) was stirred at rt for 3 hrs. The resulting reaction mixture was concentrated in vacuo to afford 5-fluoro-1,2,3,4-tetrahydroisoquinoline hydrochloride (120 mg) as a white solid, which was used in the next step without any further purification.

Step 8: Preparation of 5-fluoro-2-(2-pyrimidin-2-ylpyrimidin-5-yl)-3,4-dihydro-1H-isoquinoline

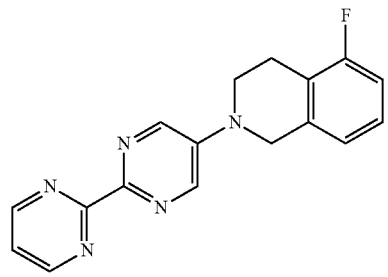 [SMILES: Fc1cccc2c1CCN(c1cnc(-c3ncccn3)nc1)C2]

To a solution of 5-fluoro-1,2,3,4-tetrahydroisoquinoline hydrochloride (110 mg, 0.59 mmol) in dioxane (2 mL) was added 5-bromo-2-pyrimidin-2-yl-pyrimidine (208 mg, 0.88 mmol, the product of step 3 in Example 1), $Cs_2CO_3$ (573 mg, 1.76 mmol) and Brettphos Pd G3 (106 mg, 0.12 mmol, CAS registry number: 1470372-59-8). The resulting mixture was stirred at 120° C. for 12 hrs. After being cooled to rt, the reaction mixture was filtered and the filtrate was concentrated in vacuo. The residue was purified by prep-HPLC to give 5-fluoro-2-(2-pyrimidin-2-ylpyrimidin-5-yl)-3,4-dihydro-1H-isoquinoline (18.5 mg) as a white solid. $^1$H NMR (400 MHz, $CDCl_3$) δ ppm: 8.96 (d, 2H), 8.63 (s, 2H), 7.33 (t, 1H), 7.15-7.26 (m, 1H), 7.04 (d, 1H), 6.97 (t, 1H), 4.59 (s, 2H), 3.75 (t, 2H), 3.05 (t, 2H). MS obsd. (ESI$^+$) [(M+H)$^+$]: 308.

Example 28

2-[[5-Fluoro-2-(2-pyrimidin-2-ylpyrimidin-5-yl)-3,4-dihydro-1H-isoquinolin-7-yl]oxy]acetamide

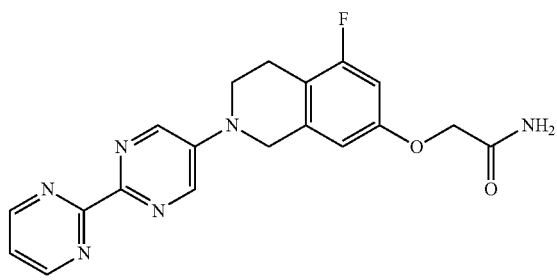 [SMILES: NC(=O)COc1cc(F)c2c(c1)CN(c1cnc(-c3ncccn3)nc1)CC2]

A mixture of 5-fluoro-2-(2-pyrimidin-2-ylpyrimidin-5-yl)-3,4-dihydro-1H-isoquinolin-7-ol (100 mg, 0.31 mmol, the product of step 1 in Example 19), 2-bromoacetamide (51 mg, 0.37 mmol) and potassium carbonate (64 mg, 0.46 mmol) in DMF (2 mL) was stirred at 70° C. for 16 hrs. The resulting mixture was cooled to rt and filtered. The filtrate was purified by prep-HPLC to give 2-[[5-fluoro-2-(2-pyrimidin-2-ylpyrimidin-5-yl)-3,4-dihydro-1H-isoquinolin-7-yl]oxy]acetamide (17 mg) as a white solid. $^1$H NMR (400 MHz, Methanol-$d_4$) δ ppm: 8.95 (br d, 2H), 8.68 (s, 2H), 7.53 (t, 1H), 6.79 (s, 1H), 6.71 (dd, 1H), 4.65 (s, 2H), 4.52 (s, 2H), 3.81 (t, 2H), 2.94 (t, 2H). MS obsd. (ESI$^+$) [(M+H)$^+$]: 381.

Example 29

5-Cyclopropyl-2-(2-pyrimidin-2-ylpyrimidin-5-yl)-3,4-dihydro-1H-isoquinoline

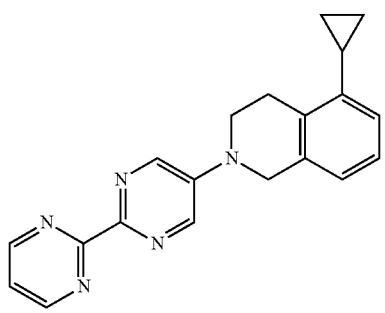 [SMILES: c1cnc(-c2ncc(N3CCc4c(cccc4C4CC4)C3)cn2)nc1]

Step 1: Preparation of tert-butyl 5-bromo-3,4-dihydro-1H-isoquinoline-2-carboxylate

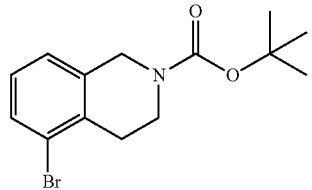 [SMILES: CC(C)(C)OC(=O)N1CCc2c(Br)cccc2C1]

To a solution of 5-bromo-1,2,3,4-tetrahydroisoquinoline (4.24 g, 20 mmol) and di-tert-butyl pyrocarbonate (5.2 g, 24 mmol) in THF (45 mL) was added TEA (4.0 g, 40 mmol) dropwise. The resulting mixture was stirred for 15 hrs at rt, then poured into water (50 mL) and extracted with EA (75 mL) twice. The organic layers were combined, then washed with water and brine, dried over anhydrous $Na_2SO_4$ and concentrated in vacuo. The residue was purified by column (eluting with PE/EA=5/1, v:v) to provide tert-butyl 5-bromo-3,4-dihydro-1H-isoquinoline-2-carboxylate (5 g) as a white solid.

Step 2: Preparation of tert-butyl 5-cyclopropyl-3,4-dihydro-1H-isoquinoline-2-carboxylate

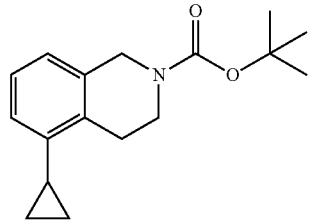 [SMILES: CC(C)(C)OC(=O)N1CCc2c(cccc2C2CC2)C1]

To a solution of tert-butyl 5-bromo-3,4-dihydro-1H-isoquinoline-2-carboxylate (1.25 g, 4 mmol) and cyclopropylboronic acid (687 mg, 8 mmol) in toluene (10 mL) was added palladium diacetate (90 mg, 0.4 mmol), tricyclohexyl phosphine (224 mg, 0.8 mmol) and potassium phosphate (1.69 g, 8 mmol). The resulting mixture was heated at 110° C. with stirring for 15 hrs. After being cooled to rt, the resulting mixture was poured into water (50 mL) and extracted with EA (50 mL) twice. The combined organic layer was washed with water and brine, then dried over anhydrous $Na_2SO_4$ and concentrated in vacuo. The residue was purified by column (eluting with PE/EA=5/1, v:v) to tert-butyl 5-cyclopropyl-3,4-dihydro-1H-isoquinoline-2-carboxylate (547 mg) as a white solid.

Step 3: Preparation of 5-cyclopropyl-1,2,3,4-tetrahydroisoquinoline hydrochloride

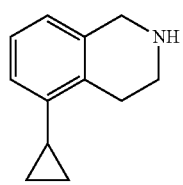 [SMILES: c1cc2c(c(C3CC3)c1)CCNC2]

To a solution of tert-butyl 5-cyclopropyl-3,4-dihydro-1H-isoquinoline-2-carboxylate (547 mg, 2 mmol) in EA (5 mL) was added HCl (10 mL, 10 mmol, 1.0 M in EA). The resulting mixture was stirred for 3 hrs at rt and then concentrated in vacuo to give 5-cyclopropyl-1,2,3,4-tetrahydroisoquinoline hydrochloride (312 mg), which was used in the next step without any further purification.

Step 4: Preparation of 5-cyclopropyl-2-(2-pyrimidin-2-ylpyrimidin-5-yl)-3,4-dihydro-1H-isoquinoline

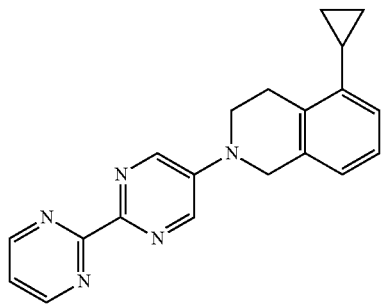 [SMILES: c1cnc(-c2ncc(N3CCc4c(cccc4C4CC4)C3)cn2)nc1]

To a solution of 5-bromo-2-pyrimidin-2-yl-pyrimidine (356 mg, 1.5 mmol, the product of step 3 in Example 1) and 5-cyclopropyl-1,2,3,4-tetrahydroisoquinoline hydrochloride (312 mg, 1.8 mmol) in dioxane (5 mL) was added Brettphos Pd G3 (62.7 mg, 0.075 mmol, CAS registry number: 1470372-59-8) and cesium carbonate (1.95 g, 6 mmol). The resulting mixture was heated at 110° C. with stirring for 15 hrs. The resulting mixture was poured into water (30 mL) and extracted with DCM (50 mL) twice. The combined organic layer was washed with water and brine, then dried over anhydrous Na$_2$SO$_4$ and concentrated in vacuo. The residue was purified by prep-HPLC to provide 5-cyclopropyl-2-(2-pyrimidin-2-ylpyrimidin-5-yl)-3,4-dihydro-1H-isoquinoline (30 mg) as an off-white powder. $^1$H NMR (400 MHz, CDCl$_3$) δ ppm: 8.98 (d, 2H), 8.65 (s, 2H), 7.35 (t, 1H), 7.15-7.22 (m, 1H), 7.09 (d, 1H), 6.97-7.03 (m, 1H), 4.61 (s, 2H), 3.80 (t, 2H), 3.21 (t, 2H), 1.90 (tt, 1H), 0.85-1.03 (m, 2H), 0.60-0.72 (m, 2H). MS obsd. (ESI$^+$) [(M+H)$^+$]:330.

Example 30

N,N-Dimethyl-2-(2-pyrimidin-2-ylpyrimidin-5-yl)-3,4-dihydro-1H-isoquinolin-5-amine

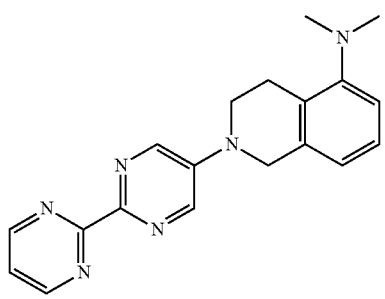 [SMILES: CN(C)c1cccc2c1CCN(c1cnc(-c3ncccn3)nc1)C2]

Step 1: Preparation of tert-butyl 5-(dimethylamino)-3,4-dihydro-1H-isoquinoline-2-carboxylate

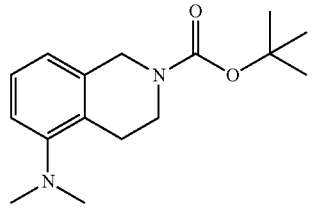 [SMILES: CN(C)c1cccc2c1CCN(C(=O)OC(C)(C)C)C2]

To a solution of tert-butyl 5-bromo-3,4-dihydro-1H-isoquinoline-2-carboxylate (212 mg, 1 mmol) and dimethyalmine hydrochloride (652 mg, 8 mmol) in 1,4-dioxane (15 mL) was added Pd$_2$(dba)$_3$ (366 mg, 0.4 mmol), RuPhos (372 mg, 0.8 mmol), and sodium tert-butoxide (1.53 g, 16 mmol). After being heated at 100° C. with stirring for 15 hrs and cooled to rt, the resulting mixture was poured into water (50 mL) and extracted with EA (50 mL) twice. The combined organic layer was washed with water and brine, then dried over anhydrous Na$_2$SO$_4$ and concentrated in vacuo. The residue was purified by column (eluting with DCM:MeOH=20:1, v:v) to provide tert-butyl 5-(dimethylamino)-3,4-dihydro-1H-isoquinoline-2-carboxylate (415 mg) as a yellow solid.

Step 2: Preparation of N,N-dimethyl-1,2,3,4-tetrahydroisoquinolin-5-amine hydrochloride

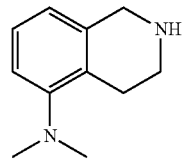

To a solution of tert-butyl 5-(dimethylamino)-3,4-dihydro-1H-isoquinoline-2-carboxylate (547 mg, 2 mmol) in EA (5 mL) was added HCl (10 mL, 1.0 M in EA). The resulting mixture was stirred for 3 hrs at rt and then concentrated in vacuo to give crude N,N-dimethyl-1,2,3,4-tetrahydroisoquinolin-5-amine hydrochloride which was used in the next step without any further purification.

Step 3: Preparation of N,N-dimethyl-2-(2-pyrimidin-2-ylpyrimidin-5-yl)-3,4-dihydro-1H-isoquinolin-5-amine

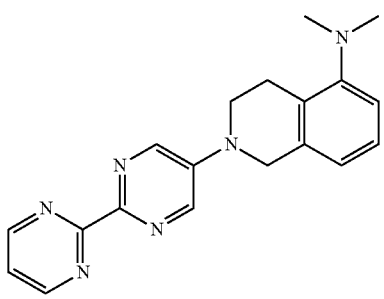 [SMILES: CN(C)c1cccc2c1CCN(c1cnc(-c3ncccn3)nc1)C2]

To a solution of 5-bromo-2-pyrimidin-2-yl-pyrimidine (356 mg, 1.5 mmol, the product of step 3 in Example 1) and N,N-dimethyl-1,2,3,4-tetrahydroisoquinolin-5-amine hydrochloride (317 mg, 1.8 mmol) in 1,4-dioxane (5 mL) was added Brettphos Pd G3 (62.7 mg, 0.075 mmol, CAS registry number: 1470372-59-8) and cesium carbonate (1.95 g, 6 mmol). After being heated at 110° C. with stirring for 15 hrs under N$_2$, the resulting mixture was poured into water (30 mL) and extracted with DCM (50 mL) twice. The combined organic layer was washed with water and brine, then dried over anhydrous Na$_2$SO$_4$ and concentrated in vacuo. The residue was purified by prep-HPLC to provide N,N-dimethyl-2-(2-pyrimidin-2-ylpyrimidin-5-yl)-3,4-dihydro-1H-isoquinolin-5-amine (110 mg) as an off-white powder. $^1$H NMR (400 MHz, CDCl$_3$) δ ppm: 8.87 (d, 2H), 8.50 (s, 2H), 7.23 (t, 1H), 7.12-7.18 (m, 1H), 6.86-7.02 (m, 2H), 4.50 (s, 2H), 3.59 (t, 2H), 2.88-3.14 (m, 2H), 2.67-2.79 (s, 6H). MS obsd. (ESI$^+$) [(M+H)$^+$]:333.

Example 31

5-Chloro-7-methoxy-2-(2-pyrimidin-2-ylpyrimidin-5-yl)-3,4-dihydro-1H-isoquinoline

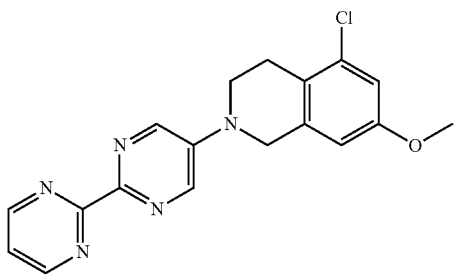

Step 1: Preparation of N-[(3-chloro-5-methoxy-phenyl)methyl]-2,2-dimethoxy-ethanamine

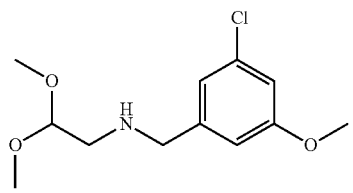 [SMILES: COc1cc(Cl)cc(CNCC(OC)OC)c1]

To a mixture of 3-chloro-5-methoxy-benzaldehyde (3.0 g, 17.59 mmol) and toluene (3 mL) was added aminoacetaldehyde dimethyl acetal (2.0 g, 19.34 mmol) and the resulting mixture was stirred at 120° C. for 5 hrs. The resulting reaction mixture was concentrated in vacuo and the residue was dissolved in MeOH (3 mL). To the solution was added NaBH$_4$ (660 mg, 17.46 mmol) at 0° C. and the reaction mixture was warmed to rt and stirred for 30 mins. Then the reaction was quenched with H$_2$O (10 mL) and the resulting mixture was extracted with EA (10 mL) for three times. The combined organic layer was washed with brine (10 mL), dried over anhydrous Na$_2$SO$_4$ and concentration in vacuo to give N-[(3-chloro-5-methoxy-phenyl)methyl]-2,2-dimethoxy-ethanamine (3.0 g, crude) which was used in the next step directly without any further purification.

Step 2: Preparation of 5-chloro-7-methoxy-1,2,3,4-tetrahydroisoquinolin-4-ol and 7-chloro-5-methoxy-1,2,3,4-tetrahydroisoquinolin-4-ol

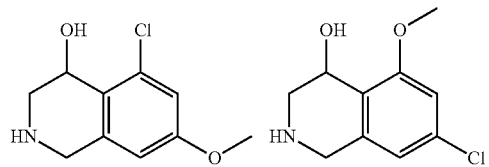

A mixture of N-[(3-chloro-5-methoxy-phenyl)methyl]-2,2-dimethoxy-ethanamine (3.0 g, crude) in HCl (30 mL, 6 M) was stirred at 40° C. for 16 hrs. The resulting mixture was concentrated in vacuo to give crude mixture of 5-chloro-7-methoxy-1,2,3,4-tetrahydroisoquinolin-4-ol and 7-chloro-5-methoxy-1,2,3,4-tetrahydroisoquinolin-4-ol (3.0 g, crude), which was used in the next step without any further purification.

Step 3: Preparation of 5-chloro-7-methoxy-1,2,3,4-tetrahydroisoquinoline and 7-chloro-5-methoxy-1,2,3,4-tetrahydroisoquinoline

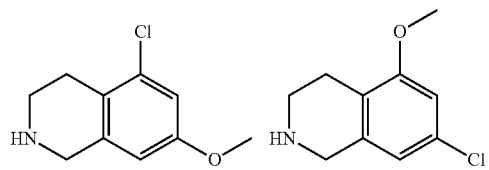

To a mixture of 5-chloro-7-methoxy-1,2,3,4-tetrahydroisoquinolin-4-ol and 7-chloro-5-methoxy-1,2,3,4-tetrahydroisoquinolin-4-ol (3.0 g, 14.04 mmol) in DCM (21 mL) was added triethylsilane (3.5 g, 30.42 mmol) and TFA (9 mL). The resulting mixture was stirred at 40° C. for 16 hrs and then concentrated in vacuo to give crude mixture of 5-chloro-7-methoxy-1,2,3,4-tetrahydroisoquinoline and 7-chloro-5-methoxy-1,2,3,4-tetrahydroisoquinoline (2.5 g, crude), which was used in the next step without any further purification.

Step 4: Preparation of tert-butyl 5-chloro-7-methoxy-3,4-dihydro-1H-isoquinoline-2-carboxylate and tert-butyl 7-chloro-5-methoxy-3,4-dihydro-1H-isoquinoline-2-carboxylate

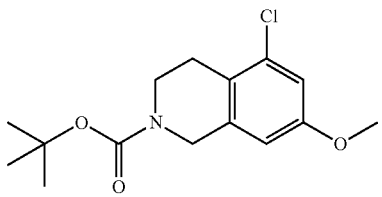

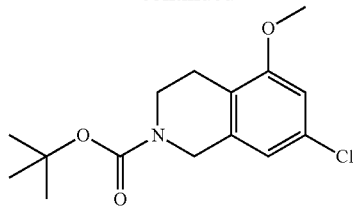

To a solution of 5-chloro-7-methoxy-1,2,3,4-tetrahydroisoquinoline and 7-chloro-5-methoxy-1,2,3,4-tetrahydroisoquinoline (2.5 g, crude mixture) in DCM (30 mL) was added TEA (11 mL, 75.89 mmol) and Boc$_2$O (4.0 g, 18.21 mmol). The resulting mixture was stirred at rt for 12 hrs and then concentrated in vacuo. The residue was dissolved in EA (30 mL). The resulting solution was washed with brine (100 mL), then dried over anhydrous Na$_2$SO$_4$ and concentrated in vacuo. The residue was purified by flash column chromatography (eluting with PE/EA=30/1, v:v) to give tert-butyl 7-chloro-5-methoxy-3,4-dihydro-1H-isoquinoline-2-carboxylate (400 mg) and tert-butyl 5-chloro-7-methoxy-3,4-dihydro-1H-isoquinoline-2-carboxylate (1.0 g).

Step 5: Preparation of 5-chloro-7-methoxy-1,2,3,4-tetrahydroisoquinoline

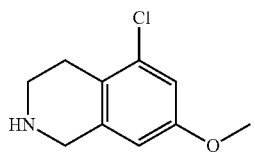

A mixture of tert-butyl 5-chloro-7-methoxy-3,4-dihydro-1H-isoquinoline-2-carboxylate (1.0 g, 3.36 mmol) and a solution of HCl in EA (20 mL, 4M) was stirred at rt for 2 hrs. The resulting mixture was concentrated in vacuo. The residue was dissolved in MeOH (3 mL) and the solution was stirred with K$_2$CO$_3$ (885 mg, 6.41 mmol) at rt for 2 hrs. The resulting mixture was filtered and the filtrate was concentrated in vacuo. The residue was dissolved in DCM (30 mL) and the solution was filtered. The filtrate was concentrated in vacuo to give 5-chloro-7-methoxy-1,2,3,4-tetrahydroisoquinoline (400 mg) as yellow oil, which was used in the next step without any further purification.

Step 6: Preparation of 5-chloro-7-methoxy-2-(2-pyrimidin-2-ylpyrimidin-5-yl)-3,4-dihydro-1H-isoquinoline

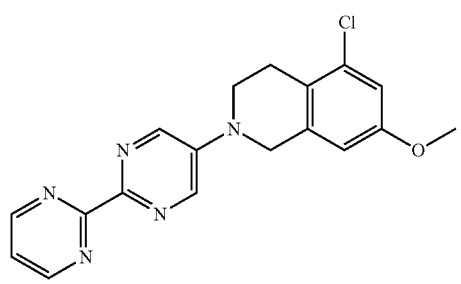

To a mixture of 5-bromo-2-pyrimidin-2-yl-pyrimidine (287 mg, 1.21 mmol, the product of step 3 in Example 1) and 5-chloro-7-methoxy-1,2,3,4-tetrahydroisoquinoline (200 mg, 1.01 mmol), Cs$_2$CO$_3$ (1.3 g, 4.05 mmol) in 1,4-dioxane (3 mL) was added Ruphos (50 mg) and Pd$_2$(dba)$_3$ (50 mg). After being stirred under N$_2$ at 120° C. for 16 hrs and cooled to rt, the resulting mixture was filtered. The filtrate was concentrated in vacuo and the residue was purified by prep-HPLC to give 5-chloro-7-methoxy-2-(2-pyrimidin-2-ylpyrimidin-5-yl)-3,4-dihydro-1H-isoquinoline (48 mg) as light yellow solid. $^1$H NMR (400 MHz, CDCl$_3$) δ ppm: 8.97 (d, 2H), 8.64 (s, 2H), 7.33-7.37 (m, 1H), 6.92 (d, 1H), 6.73 (d, 1H), 4.56 (s, 2H), 3.83 (s, 3H), 3.77 (t, 2H), 3.04 (t, 2H) MS obsd. (ESI$^+$) [(M+H)$^+$]: 354.

Example 32

7-Chloro-5-methoxy-2-(2-pyrimidin-2-ylpyrimidin-5-yl)-3,4-dihydro-1H-isoquinoline

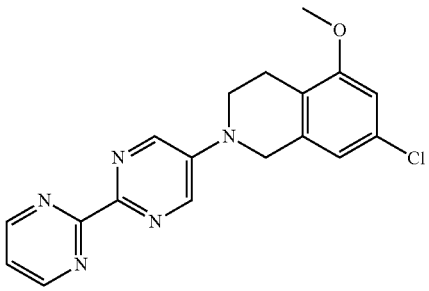 [SMILES: COc1cc(Cl)cc2c1CCN(c1cnc(-c3ncccn3)nc1)C2]

Step 1: Preparation of 7-chloro-5-methoxy-1,2,3,4-tetrahydroisoquinoline

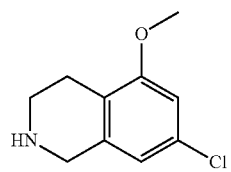

A mixture of tert-butyl 7-chloro-5-methoxy-3,4-dihydro-1H-isoquinoline-2-carboxylate (400 mg, 1.34 mmol) and a solution of HCl in EA (10 mL, 4M) was stirred at rt for 2 hrs. The resulting mixture was concentrated in vacuo and the residue was dissolved in MeOH (3 mL). To the solution was added K$_2$CO$_3$ (885 mg, 6.41 mmol). The resulting mixture was stirred at rt for 2 hrs and then filtered. The filtrate was concentrated in vacuo. The residue was dissolved in DCM (30 mL) and the solution was filtered. The filtrate was concentrated in vacuo to give 7-chloro-5-methoxy-1,2,3,4-tetrahydroisoquinoline (200 mg) as yellow solid, which was used in the next step without any further purification.

Step 2: Preparation of 7-chloro-5-methoxy-2-(2-pyrimidin-2-ylpyrimidin-5-yl)-3,4-dihydro-1H-isoquinoline

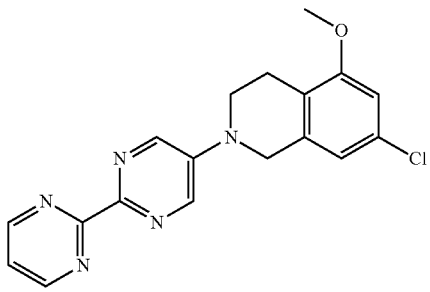 [SMILES: COc1cc(Cl)cc2c1CCN(c1cnc(-c3ncccn3)nc1)C2]

To a mixture of 5-bromo-2-pyrimidin-2-yl-pyrimidine (287 mg, 1.21 mmol, the product of step 3 in Example 1) and 7-chloro-5-methoxy-1,2,3,4-tetrahydroisoquinoline (200 mg, 1.01 mmol), $Cs_2CO_3$ (1.3 g, 4.05 mmol) in 1,4-dioxane (3 mL) was added Ruphos (50 mg) and $Pd_2(dba)_3$ (50 mg). After being stirred under $N_2$ at 120° C. for 16 hrs, the resulting reaction mixture was cooled to rt and filtered. The filtrate was concentrated in vacuo and the residue was purified by prep-HPLC to give 7-chloro-5-methoxy-2-(2-pyrimidin-2-ylpyrimidin-5-yl)-3,4-dihydro-1H-isoquinoline (28 mg) as light yellow solid. $^1$H NMR (400 MHz, $CDCl_3$) δ ppm: 8.97 (d, 2H), 8.63 (s, 2H), 7.35 (t, 1H), 6.56-6.62 (m, 2H), 4.56 (s, 2H), 3.83 (s, 3H), 3.75 (t, 2H), 2.97 (t, 2H), MS obsd ($ESI^+$) [$(M+H)^+$]: 354.

Example 33

Ethyl-5-fluoro-7-methoxy-2-(2-pyrimidin-2-ylpyrimidin-5-yl)-3,4-dihydro-1H-isoquinoline

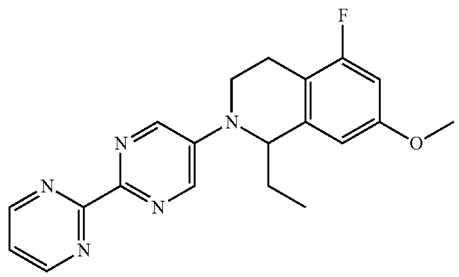

To a solution of 5-fluoro-7-methoxy-2-(2-pyrimidin-2-ylpyrimidin-5-yl)-3,4-dihydro-1H-isoquinoline (110 mg, 326 μmol, Example 5) in MeOH (5 mL) and THF (5 mL) was added NBS (116 mg, 652 μmol). The resulting mixture was stirred at rt for 2 hrs and then quenched with saturated aqueous $Na_2SO_3$ solution. The resulting mixture was extracted with DCM (30 mL) twice. The combined DCM layer was dried over anhydrous $Na_2SO_4$ and concentrated in vacuo. The residue was dissolved in THF (5 mL) and the solution was cooled to −70° C. To the cooled solution was added borontrifluoride etherate (92.6 mg, 82.6 μL2) and a solution of ethylmagnesium bromide (978 μL, 978 μmol, 1.0 M) in $Et_2O$. The resulting mixture was slowly warmed to rt and stirred for 2 hrs. The reaction was quenched by addition of $H_2O$ and the resulting mixture was extracted with DCM (30 mL) twice. The combined organic layer was dried over anhydrous $Na_2SO_4$ and concentrated in vacuo. The residue was purified by prep-HPLC to give ethyl-5-fluoro-7-methoxy-2-(2-pyrimidin-2-ylpyrimidin-5-yl)-3,4-dihydro-1H-isoquinoline (10 mg) as white solid. $^1$H NMR (400 MHz, $CDCl_3$) δ ppm: 1.06 (t, 3H), 1.80-2.12 (m, 2H), 2.80-2.94 (m, 1H), 3.04-3.17 (m, 1H), 3.66-3.79 (m, 2H), 3.82 (s, 3H), 4.65-4.81 (m, 1H), 6.56 (s, 2H), 7.33-7.45 (m, 1H), 8.50-8.76 (m, 2H), 8.89-9.15 (m, 2H). MS obsd. ($ESI^+$) [$(M+H)^+$]: 366.

BIOLOGICAL EXAMPLES

Example 34 Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells were seeded in duplicate into white, 96-well plates at $1.5 \times 10^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 μL/well culture supernatant was used and HBsAg was quantified using HBsAg chemiluminescence immunoassay (CLIA) kit (Autobio Diagnostics Co., Zhengzhou, China, Catalog number: CL0310-2), 50 μL of the supernatant was transferred to the CLIA assay plate and 50 μL of enzyme conjugate reagent was added into each well. The plates were sealed and gently agitated for 1 hour at room temperature. The supernatant-enzyme-mixture was discarded and wells were washed 6 times with 300 μL of PBS. The residual liquid was removed by plating the CLIA plate right side down on absorbent tissue paper. 25 μL of substrates A and B were added to each well. Luminance was measured using a luminometer (Mithras LB 940 Multimode Microplate Reader) after 10 minutes incubation. Dose-response curves were generated and the $IC_{50}$ value was extrapolated by using the E-WorkBook Suite (ID Business Solutions Ltd., Guildford, UK). The $IC_{50}$ was defined as the compound concentration at which HBsAg secretion was reduced by 50% compared to the no drug control.

The compounds according to formula I were tested for their capacity to inhibit HBsAg as described herein. The Examples were tested in the above assay and found to have $IC_{50}$ below 50 μM. Particular compounds of formula I were found to have $IC_{50}$ below 5.0 μM. More Particular compounds of formula I were found to have $IC_{50}$ below 0.50 μM. Results of HBsAg assay are given in Table 1.

TABLE 1

Activity data in HBsAg assay

| Example No. | IC$_{50}$ (μM) |
|---|---|
| 1 | 3.172 |
| 2 | 22.472 |
| 3 | 2.323 |
| 4 | 5.202 |
| 5 | 0.355 |
| 6 | 0.454 |
| 7 | 0.315 |
| 8 | 0.445 |
| 9 | 2.516 |
| 10 | 3.124 |
| 11 | 3.89 |
| 12 | 5.771 |
| 13 | 3.703 |
| 14 | 0.99 |
| 15 | 1.689 |
| 16 | 0.406 |
| 17 | 2.009 |
| 18 | 4.637 |
| 19 | 0.255 |
| 20 | 8.64 |
| 21 | 0.244 |
| 22 | 2.036 |
| 23 | 2.215 |
| 24 | 1.378 |
| 25 | 1.189 |
| 26 | 1.412 |
| 27 | 3.027 |
| 28 | 8.519 |
| 29 | 6.894 |
| 30 | 43.332 |
| 31 | 0.068 |
| 32 | 0.251 |
| 33 | 0.79 |

HBV DNA Assay

The assay employs real-time qPCR (TaqMan) to directly measure extracellular HBV DNA copy number in the cell supernatant. HepG2.2.15 cells were plated in 96-well microtiter plates before treatment with complete medium (DMEM, Glutamax, 10% FBS, 1% Penicillin/Streptomycin, 250 μg/mL Genetycin, final DMSO concentration is 1%). Only the interior wells were utilized to reduce "edge effects" observed during cell culture, the exterior wells were filled with complete medium to help minimize sample evaporation. The HepG2.2.15 cells were treated 1 h later with various concentrations of a test compound in duplicate (top concentration used at 5 μM, 2 μM or 0.5 μM according to the HBsAg IC50 observed, with 1/3 successive dilutions (total of 10 dilutions). Six days following the initial administration of the test compound, the cell culture supernatant was collected; DNA extraction was performed by automated system (Magnapure) and then used in a real-time qPCR/TaqMan assay to determine HBV DNA copy numbers. Antiviral activity was calculated from the reduction in HBV DNA levels (IC$_{50}$). The compounds of the present invention were tested for their capacity to inhibit HBV DNA as described herein. The Examples were tested in the above assay and found to have IC$_{50}$ below 50 μM. Results of HBV DNA assay are given in Table 2.

TABLE 2

Anti HBV DNA production activity in HepG2.2.15 cells

| Example No. | IC$_{50}$ (μM) |
|---|---|
| 8 | 0.292 |

The invention claimed is:

1. A compound of formula I,

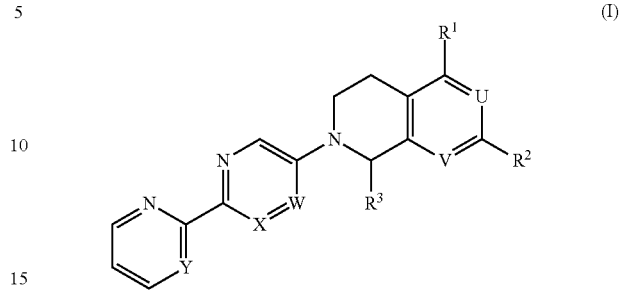

wherein:
R$^1$ and R$^2$ are independently selected from C$_{1-6}$ alkoxy, C$_{1-6}$ alkyl, C$_{1-6}$ alkylamino, C$_{3-7}$cycloalkyl, cyano, diC$_{1-6}$alkylamino, haloC$_{1-6}$alkoxy, halogen and hydrogen;
R$^3$ is C$_{1-6}$alkyl or hydrogen;
U is N or CR$^4$, wherein R$^4$ is hydrogen;
V is N or CR$^5$, wherein R$^5$ is hydrogen;
W is CH; and
X and Y are N;
or a pharmaceutically acceptable salt, enantiomer, or diastereomer thereof.

2. A compound according to claim 1, wherein:
R$^1$ and R$^2$ are independently selected from C$_{1-6}$ alkoxy, C$_{1-6}$ alkyl, C$_{1-6}$ alkylamino, C$_{3-7}$cycloalkyl, cyano, diC$_{1-6}$alkylamino, haloC$_{1-6}$alkoxy, halogen and hydrogen; and
R$^3$ is C$_{1-6}$ alkyl or hydrogen; or a pharmaceutically acceptable salt, enantiomer, or diastereomer thereof.

3. A compound according to claim 1, wherein:
R$^1$ and R$^2$ are independently selected from methoxy, methoxycyclobutyl, methyl, methylamino, cyclopropyl, cyclopropylmethoxy, cyano, dimethylamino, difluoroethoxy, chloro, fluoro and hydrogen; and
R$^3$ is ethyl, methyl or hydrogen; or a pharmaceutically acceptable salt, enantiomer, or diastereomer thereof.

4. A compound according to claim 1, or a pharmaceutically acceptable salt, enantiomer, or diastereomer thereof, wherein R$^1$ is C$_{1-6}$ alkoxy, halogen or hydrogen.

5. A compound according to claim 1, or a pharmaceutically acceptable salt, enantiomer, or diastereomer thereof, wherein R$^1$ is methoxy, chloro, fluoro or hydrogen.

6. A compound according to claim 1, or a pharmaceutically acceptable salt, enantiomer, or diastereomer thereof, wherein R$^2$ is C$_{1-6}$ alkoxy, C$_{3-7}$cycloalkylC$_{1-6}$alkoxy, haloC$_{1-6}$alkoxy, halogen or hydrogen.

7. A compound according to claim 1, or a pharmaceutically acceptable salt, enantiomer, or diastereomer thereof, wherein R$^2$ is methoxy, cyclopropylmethoxy, difluoroethoxy, chloro, fluoro or hydrogen.

8. A compound according to claim 1, or a pharmaceutically acceptable salt, enantiomer, or diastereomer thereof, wherein R$^3$ is hydrogen.

9. A compound according to claim 1, or a pharmaceutically acceptable salt, enantiomer, or diastereomer thereof, wherein U is CH; V is CH; X is N; and Y is N.

10. A compound according to claim 1, wherein:
R$^1$ is C$_{1-6}$ alkoxy or halogen;
R$^2$ is C$_{1-6}$ alkoxy, C$_{3-7}$ cycloalkylC$_{1-6}$ alkoxy, haloC$_{1-6}$alkoxy or halogen;

$R^3$ is $C_{1-6}$ alkyl or hydrogen;
U is CH; and
V is CH;
or a pharmaceutically acceptable salt, enantiomer, or diastereomer thereof.

11. A compound according to claim 1, wherein:
$R^1$ is methoxy, chloro or fluoro;
$R^2$ is methoxy, cyclopropylmethoxy, difluoroethoxy or chloro;
$R^3$ is methyl or hydrogen;
U is CH; and
V is CH;
or a pharmaceutically acceptable salt, enantiomer, or diastereomer thereof.

12. A compound according to claim 1, selected from:
2-(2-Pyrimidin-2-ylpyrimidin-5-yl)-3,4-dihydro-1H-isoquinoline;
7-Fluoro-2-(2-pyrimidin-2-ylpyrimidin-5-yl)-3,4-dihydro-1H-isoquinoline;
5-Fluoro-7-methoxy-2-(2-pyrimidin-2-ylpyrimidin-5-yl)-3,4-dihydro-1H-isoquinoline;
7-Fluoro-5-methoxy-2-(2-pyrimidin-2-ylpyrimidin-5-yl)-3,4-dihydro-1H-isoquinoline;
5-Fluoro-7-methoxy-1-methyl-2-(2-pyrimidin-2-ylpyrimidin-5-yl)-3,4-dihydro-1H-isoquinoline;
2-Methoxy-7-(2-pyrimidin-2-ylpyrimidin-5-yl)-6,8-dihydro-5H-1,7-naphthyridine;
7-Methoxy-2-(2-pyrimidin-2-ylpyrimidin-5-yl)-3,4-dihydro-1H-2,6-naphthyridine;
7-Methoxy-2-(2-pyrimidin-2-ylpyrimidin-5-yl)-3,4-dihydro-1H-isoquinoline;
7-Cyclopropyl-2-(2-pyrimidin-2-ylpyrimidin-5-yl)-3,4-dihydro-1H-isoquinoline;
N,N-Dimethyl-2-(2-pyrimidin-2-ylpyrimidin-5-yl)-3,4-dihydro-1H-isoquinolin-7-amine;
7-Methyl-2-(2-pyrimidin-2-ylpyrimidin-5-yl)-3,4-dihydro-1H-isoquinoline;
N-Methyl-2-(2-pyrimidin-2-ylpyrimidin-5-yl)-3,4-dihydro-1H-isoquinolin-7-amine;
7-(2,2-Difluoroethoxy)-5-fluoro-2-(2-pyrimidin-2-ylpyrimidin-5-yl)-3,4-dihydro-1H-isoquinoline;
2-(2-Pyrimidin-2-ylpyrimidin-5-yl)-3,4-dihydro-1H-isoquinoline-7-carbonitrile;
7-Chloro-2-(2-pyrimidin-2-ylpyrimidin-5-yl)-3,4-dihydro-1H-isoquinoline;
2-(2-Pyrimidin-2-ylpyrimidin-5-yl)-3,4-dihydro-1H-isoquinoline-5-carbonitrile;
5-Fluoro-2-(2-pyrimidin-2-ylpyrimidin-5-yl)-3,4-dihydro-1H-isoquinoline;
5-Cyclopropyl-2-(2-pyrimidin-2-ylpyrimidin-5-yl)-3,4-dihydro-1H-isoquinoline;
N,N-Dimethyl-2-(2-pyrimidin-2-ylpyrimidin-5-yl)-3,4-dihydro-1H-isoquinolin-5-amine;
5-Chloro-7-methoxy-2-(2-pyrimidin-2-ylpyrimidin-5-yl)-3,4-dihydro-1H-isoquinoline;
7-Chloro-5-methoxy-2-(2-pyrimidin-2-ylpyrimidin-5-yl)-3,4-dihydro-1H-isoquinoline; and
1-Ethyl-5-fluoro-7-methoxy-2-(2-pyrimidin-2-ylpyrimidin-5-yl)-3,4-dihydro-1H-isoquinoline; or a pharmaceutically acceptable salt, enantiomer, or diastereomer thereof.

13. A compound selected from:
5-Fluoro-7-methoxy-2-(2-pyrimidin-2-ylpyrimidin-5-yl)-3,4-dihydro-1H-isoquinoline;
5-Fluoro-7-methoxy-1-methyl-2-(2-pyrimidin-2-ylpyrimidin-5-yl)-3,4-dihydro-1H-isoquinoline;
7-(2,2-Difluoroethoxy)-5-fluoro-2-(2-pyrimidin-2-ylpyrimidin-5-yl)-3,4-dihydro-1H-isoquinoline;
7-(Cyclopropylmethoxy)-5-fluoro-2-(2-pyrimidin-2-ylpyrimidin-5-yl)-3,4-dihydro-1H-isoquinoline;
5-Chloro-7-methoxy-2-(2-pyrimidin-2-ylpyrimidin-5-yl)-3,4-dihydro-1H-isoquinoline; and
7-Chloro-5-methoxy-2-(2-pyrimidin-2-ylpyrimidin-5-yl)-3,4-dihydro-1H-isoquinoline; or a pharmaceutically acceptable salt, enantiomer, or diastereomer thereof.

14. A compound selected from:
2-[[5-Fluoro-2-(2-pyrimidin-2-ylpyrimidin-5-yl)-3,4-dihydro-1H-isoquinolin-7-yl]oxy]acetamide;
7-(3-Methoxycyclobutyl)-2-(2-pyrimidin-2-ylpyrimidin-5-yl)-3,4-dihydro-1H-isoquinoline;
6-Cyclopropyl-2-(2-pyrimidin-2-ylpyrimidin-5-yl)-3,4-dihydro-1H-isoquinoline;
N,N-Dimethyl-2-(2-pyrimidin-2-ylpyrimidin-5-yl)-3,4-dihydro-1H-isoquinolin-6-amine;
6,7-Dimethoxy-2-[6-(2-pyridyl)-3-pyridyl]-3,4-dihydro-1H-isoquinoline;
6-Chloro-2-(2-pyrimidin-2-ylpyrimidin-5-yl)-3,4-dihydro-1H-isoquinoline;
5-Fluoro-7-methoxy-2-(5-pyrimidin-2-ylpyrazin-2-yl)-3,4-dihydro-1H-isoquinoline;
6,7-Dimethoxy-2-(2-pyrimidin-2-ylpyrimidin-5-yl)-3,4-dihydro-1H-isoquinoline; and
6-Methoxy-2-(2-pyrimidin-2-ylpyrimidin-5-yl)-3,4-dihydro-1H-isoquinoline,
or a pharmaceutically acceptable salt, enantiomer, or diastereomer thereof.

15. A process for preparing a compound according to claim 1, the process comprising:
(a) coupling a compound of formula (A)

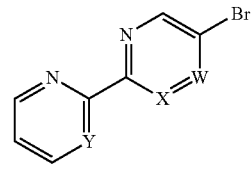

(A)

with a compound of formula (B)

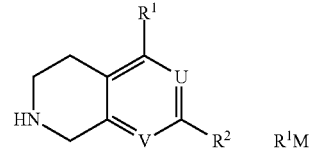

(B)

in the presence of a catalyst, a ligand and a base, to form a compound of formula B-2:

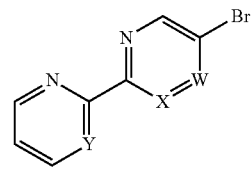

(A)

(B)

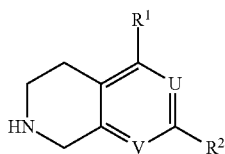

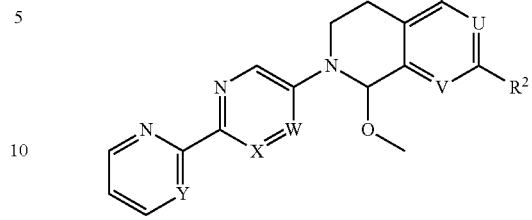
(C)

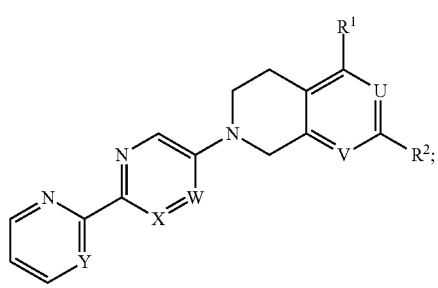
B-2

(b) oxidizing the compound of formula B-2 to give a compound of formula (C), and coupling the compound of formula (C)

with a nucleophile in the presence of a Lewis acid; wherein the nucleophile is a Grignard reagent, $R^1M$, or a dialkylzinc reagent, $(R^1)_2Zn$.

16. A compound manufactured according to the process of claim 15.

17. A pharmaceutical composition comprising the compound of claim 1 and a therapeutically inert carrier.

18. A method of inhibiting $HB_sAg$ production or secretion, or inhibiting HBV DNA production, the method comprising administering to a patient in need thereof a compound according to claim 1.

19. A method for the treatment or prophylaxis of HBV infection, which method comprises:
administering to a patient in need thereof an effective amount of a compound as defined in claim 1.

* * * * *